(12) United States Patent
Lee et al.

(10) Patent No.: US 10,077,430 B2
(45) Date of Patent: Sep. 18, 2018

(54) RECOMBINANT ADENOVIRUS WITH INCREASED SAFETY AND ANTICANCER ACTIVITIES, AND USE THEREOF

(71) Applicant: NATIONAL CANCER CENTER, Gyeonggi-do (KR)

(72) Inventors: Sang Jin Lee, Gyeonggi-do (KR); Yun-Hee Kim, Seoul (KR); In-Hoo Kim, Gyeonggi-do (KR); Seong-Wook Lee, Gyeonggi-do (KR); Jin-Sook Jeong, Busan (KR); Sang Young Han, Busan (KR)

(73) Assignee: NATIONAL CANCER CENTER, Gyeonggi-Do (KR)

( * ) Notice: Subject to any disclaimer, the term of this patent is extended or adjusted under 35 U.S.C. 154(b) by 0 days.

(21) Appl. No.: 14/646,730

(22) PCT Filed: Nov. 21, 2013

(86) PCT No.: PCT/KR2013/010639
§ 371 (c)(1),
(2) Date: May 21, 2015

(87) PCT Pub. No.: WO2014/081229
PCT Pub. Date: May 30, 2014

(65) Prior Publication Data
US 2015/0337270 A1    Nov. 26, 2015

(30) Foreign Application Priority Data

Nov. 21, 2012 (KR) .................. 10-2012-0132289

(51) Int. Cl.
| | |
|---|---|
| *C12N 15/861* | (2006.01) |
| *C12N 15/113* | (2010.01) |
| *C12N 15/33* | (2006.01) |
| *C12N 15/34* | (2006.01) |
| *C12N 15/52* | (2006.01) |
| *A61K 48/00* | (2006.01) |
| *C12N 7/00* | (2006.01) |
| *A61K 35/761* | (2015.01) |
| *A61K 38/45* | (2006.01) |
| *A61K 31/713* | (2006.01) |
| *G01N 33/574* | (2006.01) |
| *G01N 33/569* | (2006.01) |
| *C12N 15/86* | (2006.01) |

(52) U.S. Cl.
CPC .............. *C12N 7/00* (2013.01); *A61K 31/713* (2013.01); *A61K 35/761* (2013.01); *A61K 38/45* (2013.01); *A61K 48/0066* (2013.01); *C12N 15/1135* (2013.01); *C12N 15/86* (2013.01); *C12Y 207/07049* (2013.01); *G01N 33/56983* (2013.01); *G01N 33/57438* (2013.01); *C12N 2310/1241* (2013.01); *C12N 2320/32* (2013.01); *C12N 2330/51* (2013.01); *C12N 2710/10021* (2013.01); *C12N 2710/10032* (2013.01); *C12N 2710/10343* (2013.01); *C12N 2710/16633* (2013.01); *C12N 2810/6018* (2013.01); *C12N 2830/008* (2013.01); *C12N 2830/42* (2013.01); *C12N 2840/445* (2013.01); *C12Y 207/01021* (2013.01); *G01N 2333/075* (2013.01)

(58) Field of Classification Search
None
See application file for complete search history.

(56) References Cited

U.S. PATENT DOCUMENTS

| | | | | |
|---|---|---|---|---|
| 2003/0083257 A1* | 5/2003 | Negrier | ................ | C07K 14/755 514/44 R |
| 2006/0281090 A1* | 12/2006 | Lieber | ................ | C07K 14/005 435/6.16 |
| 2008/0124360 A1* | 5/2008 | Seggern | ................ | A61K 39/235 424/233.1 |
| 2011/0256524 A1* | 10/2011 | Lee | ................ | C12N 15/1135 435/5 |

FOREIGN PATENT DOCUMENTS

| | | | |
|---|---|---|---|
| JP | 2008510493 A | 4/2008 | |
| JP | 2010539923 A | 12/2010 | |

(Continued)

OTHER PUBLICATIONS

Kim et al, Image-aided Suicide Gene Therapy Utilizing Multifunctional hTERT-targeting Adenovirus for Clinical Translation in Hepatocellular Carcinoma, Theranostics 2016, vol. 6, Issue 3, pp. 357-368.*

(Continued)

*Primary Examiner* — Maria Marvich
(74) *Attorney, Agent, or Firm* — SIMI Law Group, P.C.

(57) ABSTRACT

The present invention relates to a recombinant adenovirus with increased in-vivo safety, tissue specificity, and anticancer activities, and a use thereof. Specifically, the recombinant adenovirus comprising: a promoter of the liver tissue-specific phosphoenolpyruvate carboxykinase (PEPCK) gene; a trans-splicing ribozyme which is operably linked to the promoter and acts on a cancer-specific gene; a therapeutic gene or a reporter gene which is linked to the 3' exon of the ribozyme; and a serotype 35 fiber knob and a serotype 5 shaft, in which the orf4 gene is deleted from adenovirus E1, E3 and E4 orf1, shows remarkable in-vivo safety, high specificity for a target tissue, and remarkable anticancer effects, and thus can be useful for an anticancer drug or a cancer diagnostic agent as a gene delivery vector.

8 Claims, 19 Drawing Sheets
Specification includes a Sequence Listing.

(56) References Cited

FOREIGN PATENT DOCUMENTS

| JP | 2012139220 A | 7/2012 |
|---|---|---|
| KR | 10-2007-0085254 A | 8/2007 |
| KR | 10-2010-0024055 A | 3/2010 |
| KR | 10-2011-0103119 A | 9/2011 |
| WO | 2010024483 A1 | 3/2010 |

OTHER PUBLICATIONS

Kim et al, Targeted Regression of Hepatocellular Carcinoma by Cancer-Specific RNA Replacement through MicroRNA Regulation, Scientific Reports, 2015, pp. 1-13.*

Zamboni CG, Green JJ, Higgins LJ. Local delivery of gene based therapy for hepatocellular carcinoma: the TACE of the future? Intervent Oncol 360. 2015;3(11) 1-13.*

Cho, Kyung-Sook. In Vivo Liver Toxicity of Cancer-Targeting GeneTharapy Using Trans-splicing Ribozyme, Thesis (MA), Dong-A University, Department of Medicine. 2008.

Song, Min-Sun et al., Cancer-selective induction of cytotoxicity by tissue-specific expression of targeted trans-splicing ribozyme. FEBS Letters. 2006, vol. 580, pp. 5033-5043.

Lee, Eun Jig. Targeted gene expression using adenoviral vectors. Biochemistry and Molecular Biology News. Sep. 2005, pp. 213-221.

Shayakhmetrov et al., "Analyis of Adenovirus Sequestration in the Liver, Transduction of Hepatic Cells, and Innate Toxicyt after Injection of Fiber-Modified Vectors", Journal of Virology, 2004, vol. 78, No. 10, pp. 5368-5381.

Wei Chen et al., "Enhanced antitumor efficacy of a novel fiber chimeric oncolytic adenovirus expressing p53 on hepatocellular carinom", Cancer Letters, New York, NY, US, vol. 307, No. 1, Mar. 24, 2011, pp. 93-103.

Jinyong Luo et al., "A protocol for rapid generation of recombinant adenoviruses using the AdEasy system", nature Protocols, vol. 2, No. 5, Mar. 17, 2007, pp. 1236-11247.

Ms Song et al., "Validation of tissue-specific promoter-driven tumor-targeting trans-splicing ribozyme system as multifunctional cancer gene therapy device in vivo", Cancer Gene Therapy, vol. 16, No. 2, Aug. 29, 2008, pp. 113-125.

Yun-Hee Him et al., "Image-aided suicide gene therapy utilizing multifunctional hTERT-targeting Adenovirus for Clinical Translation in Hetatocellular Caricinoma", Theranostics, vol. 6, No. 3, Jan. 1, 2016, pp. 357-368.

M.S. Song et al. Validation of tissue-specific promoter-driven tumor-targeting trans-splicing ribozyme system as a multifunctional cancer gene therapy device in vivo, Cancer Gene Therapy (2009) 16, 113-125.

B.S. Kwon et al. Specific regression of human cancer cells by ribozyme-mediated targeted replacement of tumor-specific transcript, Molecular Therapy vol. 12, No. 5, Nov. 2005.

* cited by examiner

Fig. 16
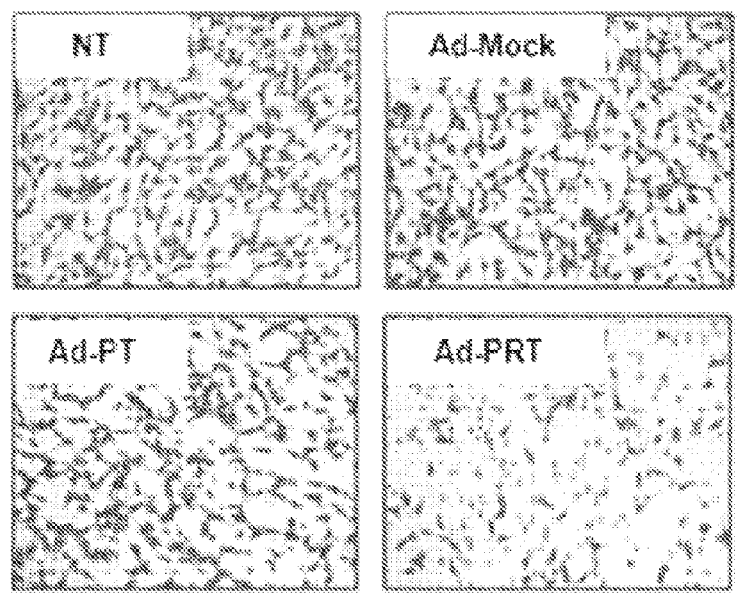
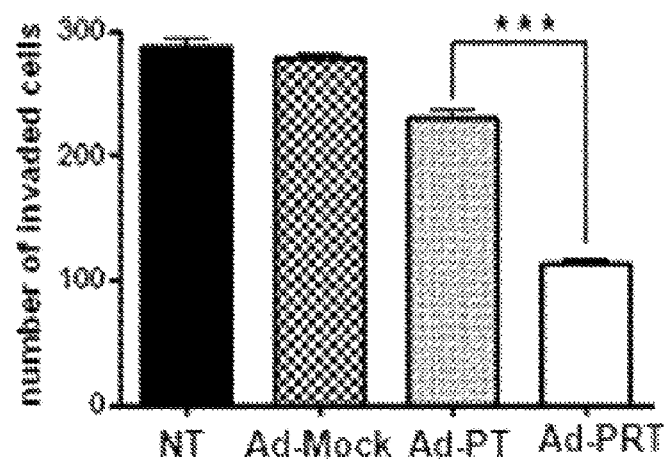

SEQUENCE LISTING

<160> NUMBER OF SEQ ID NOS: 24

<210> SEQ ID NO 1
<211> LENGTH: 2080
<212> TYPE: DNA
<213> ORGANISM: Artificial Sequence
<220> FEATURE:
<223> OTHER INFORMATION: PEPCK promoter sequence

<400> SEQUENCE: 1

| | | | | | | |
|---|---|---|---|---|---|---|
| cgagctcttt | ggggagtcct | aagagggcag | ctggcaatgg | acacctagca | gtcccttgga | 60 |
| gacttatttc | agatggagct | gtagaaagat | gccatggctc | acagtgcctc | cctgggaagg | 120 |
| gggcagaggg | ctgcccagtg | aggcctcttg | cgagcaggaa | atcaccagag | acaaggaaag | 180 |
| accagacccc | aggatgacct | cagttaggcc | ttgcccgact | gtcctcagag | tcccattctc | 240 |
| tgtgtcctgg | ttcttttaga | agatcatgga | cctccaggtc | atttcgtaac | cggaatctgc | 300 |
| cttgcgggg | gttttgacaa | gctatggtat | agtgtatgtg | ggggtactga | cgaattggaa | 360 |
| gatcatggag | acccccttctc | ctcctccatc | attggtctgc | cacatccctc | ccaggagact | 420 |
| cacagcagag | agaccttgga | tgtatgtagg | gtgctttaaa | actccagctg | agttacagtc | 480 |
| tctcctttct | gttttcacct | taaccttcca | gggatgcaaa | cccacgacag | gtttagcagc | 540 |
| agagtggagg | ctggccatga | atctcagaga | aagtgctcac | tggaaaggct | ggtttagccc | 600 |
| aggcctgatg | tggaggcact | gagctggacg | ttctagcggg | gttgacaccc | aacagtttac | 660 |
| atagggggag | gccaccccctc | ctgagcagtc | tcggtgactt | gaagaggaag | ccgcttcttc | 720 |
| tgtaccaaca | cagaagctcc | agcgaacccc | cagaatgctg | gcagtgtggg | tgctatgtaa | 780 |
| aagtattttac | atagctttgt | agagtgagcc | aagcccagtc | tgtttgggat | gactcttcac | 840 |
| agtgcctcga | atctgtcaca | cgtcttagta | agcagagtca | cagagtttct | gtcacatcat | 900 |
| cctcctgcct | acagggaagt | aggccatgtc | cctgcccccct | actctgagcc | cagctgtggg | 960 |
| agccagcccct | gcccaatggg | ctctctctga | ttgacttctc | actcacttct | aaactccagt | 1020 |
| gagcaacttc | tctcggctcg | ttcaattggc | gtgaaggtct | gtgtcttgca | gagaaggttc | 1080 |
| ttcacaactg | ggataaaggt | ctcgctgctc | aagtgtagcc | cagtagaact | gccaagcccc | 1140 |
| ttcccctcct | ctccctagac | tcttggatgc | aagaagaatc | caggcagctc | caagggtgat | 1200 |
| tgtgtccaac | ctagaatgtc | ttgaaaaaga | cattaagggg | actagagaag | acaggggatc | 1260 |
| caacggttct | ctgcagccca | gcctgactga | catgtaactc | ttctggttct | caccagccag | 1320 |
| ctggacctgc | ttagtattct | ttctgcctca | gtttcccagc | ctgtacccag | ggctgtcata | 1380 |
| gttccatttc | aggcagtagt | aatgaatgag | ctgacataaa | acatttagag | caggggtcag | 1440 |
| tatgtatata | gagtgattat | tctatatcac | gcattgcctc | ctcggaatga | agcttacaat | 1500 |
| caccccctccc | tctgcagttc | atcttggggt | ggccagagga | tccagcagac | acctagtggg | 1560 |
| gtaacacacc | ccagccaact | cggctgttgc | agactttgtc | tagaagtttc | acgtctcaga | 1620 |
| gctgaattcc | cttctcatga | cctttggccg | tgggagtgac | acctcacagc | tgtggtgttt | 1680 |
| tgacaaccag | cagccactgg | cacacaaaat | gtgcagccag | cagcatatga | agtccaagag | 1740 |
| gcgtcccggc | cagcccctgtc | cttgaccccc | acctgacaat | taaggcaaga | gcctatagtt | 1800 |
| tgcatcagca | acagtcacgg | tcaaagttta | gtcaatcaaa | cgttgtgtaa | ggactcaact | 1860 |

```
atggctgaca cgggggcctg aggcctccca acattcatta acaacagcaa gttcaatcat    1920
tatctcccca aagtttattg tgttaggtca gttccaaacc gtgctgacca tggctatgat    1980
ccaaaggccg gccccttacg tcagaggcga gcctccaggt ccagctgagg ggcagggctg    2040
tcctcccttc tgtatactat ttaaagcgag gagggctagc                          2080

<210> SEQ ID NO 2
<211> LENGTH: 310
<212> TYPE: DNA
<213> ORGANISM: Artificial Sequence
<220> FEATURE:
<223> OTHER INFORMATION: ApoA1 intron sequence

<400> SEQUENCE: 2
taccaagcac ggttggcctt ccctctggga acacaccctt ggccaacagg ggaaatccgg     60
cgagacgctc tgagatcctg cgagaaggag gtgcgtcctg ctgcctgccc cggtcactct    120
ggctccccag ctcaaggttc aggccttgcc ccaggccggg cctctgggta cctgaggtct    180
tctcccgctc tgtgcccttc tcctcacctg gctgcaatga gtggggagc acggggcttc    240 tgcatgctga aggcacccca ctcagccagg cccttcttct cctccaggtc ccccacggcc    300
cttcagatcc                                                           310

<210> SEQ ID NO 3
<211> LENGTH: 790
<212> TYPE: DNA
<213> ORGANISM: Artificial Sequence
<220> FEATURE:
<223> OTHER INFORMATION: trans-splicing ribozyme sequence

<400> SEQUENCE: 3
gtttagtgaa ccgtcagaat tgttttatt tttaattttc tttcaaatac ttccatcgaa      60
ttcagatctg cggccgcaag gccagcacgt tcttcgcgcc gcgctcgcac agcctctgca    120
gcactcgggc caccagctcc ttcaggcagg acacctggcg gaaggagggg gcggcggggg    180
gcggccgtgc gtcccagggc acgcacacca ggcactgggc caccagcgcg cggaaagccg    240
ccgggtcccc gcgctgcacc agccgccagc cctggggccc caggcgccgc acgaacgtgg    300
ccagcggcag cacctcgcgg tagtggctgc gcagcaggga gcgcacggct cggcagcggg    360
gagcgcgcgg catcgcgggg gtggccgggg ccagggcttc ccaagcttcg ttttgcggca    420
ggaaaagtta tcaggcatgc acctggtagc tagtctttaa accaatagat tgcatcggtt    480
taaaaggcaa gaccgtcaaa ttgcgggaaa ggggtcaaca gccgttcagt accaagtctc    540 agggggaaact ttgagatggc cttgcaaagg gtatggtaat aagctgacgg acatggtcct    600
aaccacgcag ccaagtccta agtcaacaga tcttctgttg atatggatgc agttcacaga    660
ctaaatgtcg gtcggggaag atgtattctt ctcataagat atagtcggac ctctccttaa    720
tgggagctag cggatgaagt gatgcaacac tggagccgct gggaactaat ttgtatgcga    780
aagtatattg                                                           790

<210> SEQ ID NO 4
<211> LENGTH: 1127
<212> TYPE: DNA
<213> ORGANISM: Artificial Sequence
<220> FEATURE:
<223> OTHER INFORMATION: HSVtk sequence

<400> SEQUENCE: 4
atggcttcgt accccctgcca tcaacacgcg tctgcgttcg accaggctgc gcgttctcgc     60
```

| | |
|---|---|
| ggccatagca accgacgtac ggcgttgcgc cctcgccggc agcaagaagc cacggaagtc | 120 |
| cgcctggagc agaaaatgcc cacgctactg cgggtttata tagacggtcc tcacgggatg | 180 |
| gggaaaacca ccaccacgca actgctggtg gccctgggtt cgcgcgacga tatcgtctac | 240 |
| gtacccgagc cgatgactta ctggcaggtg ctggggggctt ccgagacaat cgcgaacatc | 300 |
| tacaccacac aacaccgcct cgaccagggt gagatatcgg ccggggacgc ggcggtggta | 360 |
| atgacaagcg cccagataac aatgggcatg cctta tgccg tgaccgacgc cgttctggct | 420 |
| cctcatatcg gggggaggc tgggagctca catgccccgc ccccggccct caccctcatc | 480 |
| ttcgaccgcc atcccatcgc cgccctcctg tgctacccgg ccgcgcgata ccttatgggc | 540 |
| agcatgaccc cccaggccgt gctggcgttc gtggccctca tcccgccgac cttgcccggc | 600 |
| acaaacatcg tgttgggggc ccttccggag gacagacaca tcgaccgcct ggccaaacgc | 660 |
| cagcgccccg gcgagcggct tgacctggct atgctggccg cgattcgccg cgtttacggg | 720 |
| ctgcttgcca atacggtgcg gtatctgcag ggcggcgggt cgtggcggga ggattgggga | 780 |
| cagctttcgg ggacggccgt gccgccccag ggtgccgagc cccagagcaa cgcgggccca | 840 |
| cgaccccata tcggggacac gttatttacc ctgtttcggg cccccgagtt gctgccccc | 900 |
| aacgcgacc tgtacaacgt gtttgcctgg gccttggacg tcttggccaa acgcctccgt | 960 |
| cccatgcacg tctttatcct ggattacgac caatcgcccg ccggctgccg ggacgccctg | 1020 |
| ctgcaactta cctccgggat ggtccagacc cacgtcacca cccccggctc cataccgacg | 1080 |
| atctgcgacc tggcgcgcac gtttgcccgg gagatggggg aggctaa | 1127 |

<210> SEQ ID NO 5
<211> LENGTH: 630
<212> TYPE: DNA
<213> ORGANISM: Artificial Sequence
<220> FEATURE:
<223> OTHER INFORMATION: poly A signal sequence

<400> SEQUENCE: 5

| | |
|---|---|
| ctgaagcttg cggccgcggt ggcatccctg tgacccctcc ccagtgcctc tcctggccct | 60 |
| ggaagttgcc actccagtgc ccaccagcct tgtcctaata aaattaagtt gcatcatttt | 120 |
| gtctgactag gtgtccttct ataatattat ggggtggagg ggggtggtat ggagcaaggg | 180 |
| gcaagttggg aagacaacct gtagggcctg cggggtctat tgggaaccaa gctggagtgc | 240 |
| agtggcacaa tcttggctca ctgcaatctc cgcctcctgg gttcaagcga ttctcctgcc | 300 |
| tcagcctccc gagttgttgg gattccaggc atgcatgacc aggctcagct aattttttgtt | 360 |
| tttttggtag agacggggtt tcaccatatt ggccaggctg gtctccaact cctaatctca | 420 |
| ggtgatctac ccaccttggc ctcccaaatt gctgggatta caggcgtgaa ccactgctcc | 480 |
| cttccctgtc cttctgattt taaaataact ataccagcag gaggacgtcc agacacagca | 540 |
| taggctacct ggccatgccc aaccggtggg acatttgagt tgcttgcttg gcactgtcct | 600 |
| ctcatgcgtt gggtccactc agtagatgcc | 630 |

<210> SEQ ID NO 6
<211> LENGTH: 1683
<212> TYPE: DNA
<213> ORGANISM: Artificial Sequence
<220> FEATURE:
<223> OTHER INFORMATION: ApoE enhancer sequence

<400> SEQUENCE: 6

```
tgcaggctca gaggcacaca ggagtttctg ggctcaccct gccccttcc aacccctcag      60
ttcccatcct ccagcagctg tttgtgtgct gcctctgaag tccacactga acaaacttca    120
gcctactcat gtccctaaaa tgggcaaaca ttgcaagcag caaacagcaa acacacagcc    180
ctccctgcct gctgaccttg gagctggggc agaggtcaga gacctctctg ggcccatgcc    240
acctccaaca tccactcgac cccttggaat tcggtggag aggagcagag gttgtcctgg     300
cgtggtttag gtagtgtgag agggtccggg ttcaaaacca cttgctgggt ggggagtcgt    360
cagtaagtgg ctatgccccg accccgaagc ctgtttcccc atctgtacaa tggaaatgat    420
aaagacgccc atctgatagg gttttttgtgg caaataaaca tttggttttt ttgttttgtt    480
ttgttttgtt ttttgagatg gaggtttgct ctgtcgccca ggctggagtg cagtgacaca    540
atctcatctc accacaacct tcccctgcct cagcctccca gtagctggga ttacaagca     600
tgtgccacca cacctggcta attttctatt tttagtagag acgggtttct ccatgttggt    660
cagcctcagc ctcccaagta actgggatta caggcctgtg ccaccacacc cagctaattt    720
tttctatttt tgacagggac ggggtttcac catgttggtc aggctggtct agaactcctg    780
acctcaaatg atccacccac ctaggcctcc caaagtgcac agattacagg cgtgggccac    840
cgcacctggc caaattttta attttttcct agagataggg tcttactgtg ttgcccaggc    900
tggtgtcaaa ctcctgggct caagcagatc ctcctgcctc agcttcccaa agtggtggga    960
ttataggtgt gagccactgc gcccagtcag tagcccccctc tttgcccctc actgagccct   1020
actggatgtt cttggttgtg tgacagtttc cccatctatt aaacagaaac ccctatagca   1080
gaggggagga tgaggttgga aaatcaggag cattgttatt ctattcttgt gggatcgggg   1140
aagcagacat ctgggtggat gtttggggaa tgctgggctc agttgaggaa gtagggggc    1200
ccctgggggct tacagggact ggaagctctg agctggccag agggatgttg caatcctgcc   1260
agggtcttgt ctatgctgtc cctttcacaa ccatccccct accgccaggc tgacacgtgg   1320
ttgtgggggc acaaggccag ccgaactaga gtctgaggct gggctgagga cacctcccc    1380
atcagctgcc agggtcactg gcggtcaaag gcagctggtg gggaaggaat tggactccag   1440
ccctggggga cggatgtggt gatggtggga agcaggcttg gtgccaggag gggcatcaga   1500
gggtgaataa gagcagatag agtgtttggg ggaggtagcc agccaaaggg ggtgaggccc   1560
ggtgaaggg aagaagggc atacactcag agctttgcag ctgaaggttt taattttttg    1620
agatggggtc tcactctgtc tcaccaggct ggagtgcagt ggcgcaatca cagctcactg   1680
cag                                                                 1683
```

<210> SEQ ID NO 7
<211> LENGTH: 36
<212> TYPE: DNA
<213> ORGANISM: Artificial Sequence
<220> FEATURE:
<223> OTHER INFORMATION: forward primer for ribozyme

<400> SEQUENCE: 7
acgtatggat ccgtttagtg aaccgtcaga attgtt      36

<210> SEQ ID NO 8
<211> LENGTH: 34
<212> TYPE: DNA
<213> ORGANISM: Artificial Sequence
<220> FEATURE:
<223> OTHER INFORMATION: reverse primer for ribozyme

<400> SEQUENCE: 8
acgtatgtta actttcgagt actccaaaac taat                                34

<210> SEQ ID NO 9
<211> LENGTH: 24
<212> TYPE: DNA
<213> ORGANISM: Artificial Sequence
<220> FEATURE:
<223> OTHER INFORMATION: AdITR forward primer

<400> SEQUENCE: 9
agccaatatg ataatcaggg ggtg                                           24

<210> SEQ ID NO 10
<211> LENGTH: 22
<212> TYPE: DNA
<213> ORGANISM: Artificial Sequence
<220> FEATURE:
<223> OTHER INFORMATION: AdITR reverse primer

<400> SEQUENCE: 10
tacgcgctat gagtaacaca aa                                             22

<210> SEQ ID NO 11
<211> LENGTH: 20
<212> TYPE: DNA
<213> ORGANISM: Artificial Sequence
<220> FEATURE:
<223> OTHER INFORMATION: HSVtk specific forward primer

<400> SEQUENCE: 11
gcgaacatct acaccacaca                                                20

<210> SEQ ID NO 12
<211> LENGTH: 19
<212> TYPE: DNA
<213> ORGANISM: Artificial Sequence
<220> FEATURE:
<223> OTHER INFORMATION: HSVtk specific reverse primer

<400> SEQUENCE: 12
agttagcctc ccccatctc                                                 19

<210> SEQ ID NO 13
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 13
tgacatcaag aaggtggtga                                                20

<210> SEQ ID NO 14
<211> LENGTH: 20
<212> TYPE: DNA
<213> ORGANISM: Artificial Sequence
<220> FEATURE:
<223> OTHER INFORMATION: GAPDH reversse primer

<400> SEQUENCE: 14
tccaccaccc tgttgctgta                                                20

<210> SEQ ID NO 15
<211> LENGTH: 26
<212> TYPE: DNA

```
<213> ORGANISM: Artificial Sequence
<220> FEATURE:
<223> OTHER INFORMATION: HSVtk specific primer

<400> SEQUENCE: 15
cgggatcctc agttagcctc ccccat                                              26

<210> SEQ ID NO 16
<211> LENGTH: 25
<212> TYPE: DNA
<213> ORGANISM: Artificial Sequence
<220> FEATURE:
<223> OTHER INFORMATION: hTERT RNA specific primer

<400> SEQUENCE: 16
ggggaattca gcgctgcgtc ctgct                                               25

<210> SEQ ID NO 17
<211> LENGTH: 20
<212> TYPE: DNA
<213> ORGANISM: Artificial Sequence
<220> FEATURE:
<223> OTHER INFORMATION: HSV-tk specific primer

<400> SEQUENCE: 17
gttatctggg cgcttgtcaa                                                     20

<210> SEQ ID NO 18
<211> LENGTH: 18
<212> TYPE: DNA
<213> ORGANISM: Artificial Sequence
<220> FEATURE:
<223> OTHER INFORMATION: 5' primer specific for the trans-splicing
      junction

<400> SEQUENCE: 18
gctgcgtcct gctaaaac                                                       18

<210> SEQ ID NO 19
<211> LENGTH: 20
<212> TYPE: DNA
<213> ORGANISM: Artificial Sequence
<220> FEATURE:
<223> OTHER INFORMATION: nested 3' primer specific to the HSV-tk

<400> SEQUENCE: 19
cagtagcgtg ggcattttct                                                     20

<210> SEQ ID NO 20
<211> LENGTH: 25
<212> TYPE: DNA
<213> ORGANISM: Artificial Sequence
<220> FEATURE:
<223> OTHER INFORMATION: hTERT RNA forward primer

<400> SEQUENCE: 20
ggggaattca gcgctgcgtc ctgct                                               25

<210> SEQ ID NO 21
<211> LENGTH: 20
<212> TYPE: DNA
<213> ORGANISM: Artificial Sequence
<220> FEATURE:
<223> OTHER INFORMATION: HSV-tk reverse primer

<400> SEQUENCE: 21
```

```
gttatctggg cgcttgtcaa                                              20

<210> SEQ ID NO 22
<211> LENGTH: 21
<212> TYPE: DNA
<213> ORGANISM: Artificial Sequence
<220> FEATURE:
<223> OTHER INFORMATION: forward primer for an internal sequence of
      HSVtk

<400> SEQUENCE: 22
cgtcctgcta aagttggccg c                                            21

<210> SEQ ID NO 23
<211> LENGTH: 20
<212> TYPE: DNA
<213> ORGANISM: Artificial Sequence
<220> FEATURE:
<223> OTHER INFORMATION: reverse primer for an internal sequence of
      HSVtk

<400> SEQUENCE: 23
gcagttgcgt ggtggtggtt                                              20

<210> SEQ ID NO 24
<211> LENGTH: 6648
<212> TYPE: DNA
<213> ORGANISM: Artificial Sequence
<220> FEATURE:
<223> OTHER INFORMATION: PEPCK_APO intron-ribozyme_HSVtk sequence

<400> SEQUENCE: 24
cgagctcttt ggggagtcct aagagggcag ctggcaatgg acacctagca gtcccttga     60 gacttatttc agatggagct gtagaaagat gccatggctc acagtgcctc cctgggaagg    120
gggcagaggg ctgcccagtg aggcctcttg cgagcaggaa atcaccagag acaaggaaag    180
accagacccc aggatgacct cagttaggcc ttgcccgact gtcctcagag tcccattctc    240
tgtgtcctgg ttcttttaga agatcatgga cctccaggtc atttcgtaac cggaatctgc    300
cttgcggggg gttttgacaa gctatggtat agtgtatgtg ggggtactga cgaattggaa    360
gatcatggag accccttctc ctcctccatc attggtctgc cacatccctc ccaggagact    420
cacagcagag agaccttgga tgtatgtagg gtgctttaaa actccagctg agttacagtc    480
tctcctttct gttttcacct taaccttcca gggatgcaaa cccacgacag gtttagcagc    540
agagtggagg ctggccatga atctcagaga aagtgctcac tggaaaggct ggtttagccc    600
aggcctgatg tggaggcact gagctggacg ttctagcggg gttgacaccc aacagtttac    660 ataggggag gccacccctc ctgagcagtc tcggtgactt gaagaggaag ccgcttcttc      720
tgtaccaaca cagaagctcc agcgaacccc cagaatgctg gcagtgtggg tgctatgtaa    780
aagtatttac atagctttgt agagtgagcc aagcccagtc tgtttgggat gactcttcac    840
agtgcctcga atctgtcaca cgtcttagta agcagagtca cagagtttct gtcacatcat    900
cctcctgcct acagggaagt aggccatgtc cctgcccct actctgagcc cagctgtggg    960
agccagccct gcccaatggg ctctctctga ttgacttctc actcacttct aaactccagt   1020
gagcaacttc tctcggctcg ttcaattggc gtgaaggtct gtgtcttgca gagaaggttc   1080
ttcacaactg ggataaaggt ctcgctgctc aagtgtagcc cagtagaact gccaagcccc    1140
ttcccctcct ctccctagac tcttggatgc aagaagaatc caggcagctc caagggtgat    1200
tgtgtccaac ctagaatgtc ttgaaaaaga cattaagggg actagagaag acaggggatc    1260
```

```
caacggttct ctgcagccca gcctgactga catgtaactc ttctggttct caccagccag   1320
ctggacctgc ttagtattct ttctgcctca gtttcccagc ctgtacccag ggctgtcata   1380
gttccatttc aggcagtagt aatgaatgag ctgacataaa acatttagag cagggggtcag   1440 tatgtatata gagtgattat tctatatcac gcattgcctc ctcggaatga agcttacaat   1500 caccccctccc tctgcagttc atcttggggt ggccagagga tccagcagac acctagtggg   1560
gtaacacacc ccagccaact cggctgttgc agactttgtc tagaagtttc acgtctcaga   1620
gctgaattcc cttctcatga cctttggccg tgggagtgac acctcacagc tgtggtgttt   1680
tgacaaccag cagccactgg cacacaaaat gtgcagccag cagcatatga agtccaagag   1740
gcgtcccggc cagccctgtc cttgaccccc acctgacaat taaggcaaga gcctatagtt   1800
tgcatcagca acagtcacgg tcaaagttta gtcaatcaaa cgttgtgtaa ggactcaact   1860
atggctgaca cgggggcctg aggcctccca acattcatta acaacagcaa gttcaatcat   1920
tatctcccca aagtttattg tgttaggtca gttccaaacc gtgctgacca tggctatgat   1980
ccaaaggccg ccccttacg tcagaggcga gcctccaggt ccagctgagg ggcagggctg   2040
tcctcccttc tgtatactat ttaaagcgag gagggctagc taccaagcac ggttggcctt   2100
ccctctggga acacacccctt ggccaacagg ggaaatccgg cgagacgctc tgagatcctg   2160
cgagaaggag gtgcgtcctg ctgcctgccc cggtcactct ggctcccag ctcaaggttc   2220 aggccttgcc ccaggccggg cctctgggta cctgaggtct tctcccgctc tgtgcccttc   2280
tcctcacctg gctgcaatga gtgggggagc acggggcttc tgcatgctga aggcaccccca   2340 ctcagccagg cccttcttct cctccaggtc ccccacggcc cttcagatcc gtttagtgaa   2400
ccgtcagaat tgtttttatt tttaattttc tttcaaatac ttccatcgaa ttcagatctg   2460
cggccgcaag gccagcacgt tcttcgcgcc gcgctcgcac agcctctgca gcactcgggc   2520
caccagctcc ttcaggcagg acacctggcg gaaggagggg gcggcggggg gcggccgtgc   2580
gtcccagggc acgcacacca ggcactgggc caccagcgcg cggaaagccg ccgggtcccc   2640
gcgctgcacc agccgccagc cctggggccc caggcgccgc acgaacgtgg ccagcggcag   2700
cacctcgcgg tagtggctgc gcagcaggga gcgcacggct cggcagcggg gagcgcgcgg   2760
catcgcgggg gtggccgggg ccagggcttc ccaagcttcg ttttgcggca ggaaaagtta   2820
tcaggcatgc acctggtagc tagtcttaa accaatagat tgcatcggtt taaaaggcaa   2880
gaccgtcaaa ttgcgggaaa ggggtcaaca gccgttcagt accaagtctc aggggaaact   2940
ttgagatggc cttgcaaagg gtatggtaat aagctgacgg acatggtcct aaccacgcag   3000
ccaagtccta agtcaacaga tcttctgttg atatggatgc agttcacaga ctaaatgtcg   3060 gtcgggaag atgtattctt ctcataagat atagtcggac ctctccttaa tgggagctag   3120
cggatgaagt gatgcaacac tggagccgct gggaactaat ttgtatgcga agtatattg   3180 attagtttg gagtactcga aaggtgccat ggcttcgtac ccctgccatc aacacgcgtc   3240
tgcgttcgac caggctgcgc gttctcgcgg ccatagcaac cgacgtacgg cgttgcgccc   3300
tcgccggcag caagaagcca cggaagtccg cctggagcag aaaatgccca cgctactgcg   3360
ggtttatata gacggtcctc acgggatggg gaaaaccacc accacgcaac tgctggtggc   3420
cctgggttcg cgcgacgata tcgtctacgt acccgagccg atgacttact ggcaggtgct   3480
gggggcttcc gagacaatcg cgaacatcta caccacacaa caccgcctcg accagggtga   3540
gatatcggcc ggggacgcgg cggtggtaat gacaagcgcc cagataacaa tgggcatgcc   3600
```

-continued

```
ttatgccgtg accgacgccg ttctggctcc tcatatcggg ggggaggctg ggagctcaca    3660
tgccccgccc ccggccctca ccctcatctt cgaccgccat cccatcgccg ccctcctgtg    3720
ctacccggcc gcgcgatacc ttatgggcag catgaccccc caggccgtgc tggcgttcgt    3780
ggccctcatc ccgccgacct tgccggcac aaacatcgtg ttgggggccc ttccggagga    3840
cagacacatc gaccgcctgg ccaaacgcca gcgccccggc gagcggcttg acctggctat    3900
gctggccgcg attcgccgcg tttacggct gcttgccaat acggtgcggt atctgcaggg    3960
cggcgggtcg tggcgggagg attggggaca gctttcgggg acggccgtgc cgccccaggg    4020
tgccgagccc cagagcaacg cgggcccacg accccatatc ggggacacgt tatttaccct    4080
gtttcgggcc cccgagttgc tggcccccaa cggcgacctg tacaacgtgt ttgcctgggc    4140
cttggacgtc ttggccaaac gcctccgtcc catgcacgtc tttatcctgg attacgacca    4200
atcgcccgcc ggctgccggg acgccctgct gcaacttacc tccgggatgg tccagaccca    4260
cgtcaccacc cccggctcca taccgacgat ctgcgacctg gcgcgcacgt ttgcccggga    4320
gatgggggag gctaactgaa gcttgcgcc gcggtggcat ccctgtgacc cctccccagt    4380
gcctctcctg gccctggaag ttgccactcc agtgcccacc agccttgtcc taataaaatt    4440
aagttgcatc attttgtctg actaggtgtc cttctataat attatgggt ggagggggt    4500
ggtatggagc aaggggcaag ttgggaagac aacctgtagg gcctgcgggg tctattggga    4560
accaagctgg agtgcagtgg cacaatcttg gctcactgca atctccgcct cctgggttca    4620
agcgattctc ctgcctcagc ctcccgagtt gttgggattc caggcatgca tgaccaggct    4680
cagctaatt ttgttttttt ggtagagacg gggtttcacc atattggcca ggctggtctc    4740
caactcctaa tctcaggtga tctacccacc ttggcctccc aaattgctgg gattacaggc    4800
gtgaaccact gctcccttcc ctgtccttct gattttaaaa taactatacc agcaggagga    4860
cgtccagaca cagcataggc tacctggcca tgcccaaccg gtgggacatt tgagttgctt    4920
gcttggcact gtcctctcat gcgttgggtc cactcagtag atgcctgcag gctcagaggc    4980
acacaggagt tctgggctc accctgcccc cttccaaccc ctcagttccc atcctccagc    5040
agctgtttgt gtgctgcctc tgaagtccac actgaacaaa cttcagccta tcatgtccc    5100
taaaatgggc aaacattgca agcagcaaac agcaaacaca cagccctccc tgcctgctga    5160
ccttggagct ggggcagagg tcagagacct ctctgggccc atgccacctc caacatccac    5220
tcgacccctt ggaatttcgg tggagaggag cagaggttgt cctggcgtgg tttaggtagt    5280
gtgagagggt ccgggttcaa aaccacttgc tgggtgggga gtcgtcagta agtggctatg    5340
ccccgacccc gaagcctgtt tccccatctg tacaatggaa atgataaaga cgcccatctg    5400
atagggtttt tgtggcaaat aaacatttgg ttttttgtt ttgtttgtt ttgttttttg    5460
agatggaggt ttgctctgtc gcccaggctg gagtgcagtg acacaatctc atctcaccac    5520
aaccttcccc tgcctcagcc tcccaagtag ctgggattac aagcatgtgc caccacacct    5580
ggctaattt ctatttttag tagagacggg tttctccatg ttggtcagcc tcagcctccc    5640
aagtaactgg gattacaggc ctgtgccacc acacccagct aatttttct attttgaca    5700
gggacgggt tcaccatgt tggtcaggct ggtctagaac tcctgacctc aaatgatcca    5760
cccacctagg cctcccaaag tgcacagatt acaggcgtgg gccaccgcac ctggccaaat    5820
tttaatttt tttctagaga tagggtctta ctgtgttgcc caggctggtg tcaaactcct    5880
gggctcaagc agatcctcct gcctcagctt cccaaagtgg tgggattata ggtgtgagcc    5940
actgcgccca gtcagtagcc ccctctttgc ccctcactga gccctactgg atgttcttgg    6000
```

```
ttgtgtgaca gtttccccat ctattaaaca gaaacccta tagcagaggg gaggatgagg    6060
ttggaaaatc aggagcattg ttattctatt cttgtgggat cggggaagca gacatctggg    6120
tggatgtttg gggaatgctg ggctcagttg aggaagtagg ggggccctg gggcttacag    6180 ggactggaag ctctgagctg gccagaggga tgttgcaatc ctgccagggt cttgtctatg    6240
ctgtcccttt cacaaccatc cccctaccgc caggctgaca cgtggttgtg ggggcacaag    6300
gccagccgaa ctagagtctg aggctgggct gaggacaccc tccccatcag ctgccagggt    6360
cactggcggt caaaggcagc tggtgggaa ggaattggac tccagccctg ggggacggat    6420
gtggtgatgg tgggaagcag gcttggtgcc aggaggggca tcagagggtg aataagagca    6480
gatagagtgt ttgggggagg tagccagcca aaggggggtga ggcccggtgg aagggaagaa    6540
ggggcataca ctcagagctt tgcagctgaa ggttttaatt ttttgagatg gggtctcact    6600
ctgtctcacc aggctggagt gcagtggcgc aatcacagct cactgcag                6648
```

RECOMBINANT ADENOVIRUS WITH INCREASED SAFETY AND ANTICANCER ACTIVITIES, AND USE THEREOF

CROSS REFERENCE TO RELATED APPLICATIONS AND CLAIM OF PRIORITY

This patent application is a National Phase application under 35 U.S.C. § 371 of International Application No. PCT/KR2013/010639, filed Nov. 21, 2013, which claims the priority based on KR 10-2012-0132289 filed Nov. 21, 2012, entire contents of which are incorporated herein by reference.

TECHNICAL FIELD

The present invention relates to a recombinant adenovirus which includes a liver tissue-specific phosphoenolpyruvate carboxykinase (PEPCK) gene promoter, a trans-splicing ribozyme operably linked to the promoter and acting on a cancer-specific gene, a therapeutic gene or reporter gene linked to the 3' exon of the ribozyme, and a serotype 35 fiber knob and serotype 5 shaft, and which lacks adenovirus E1, E3 and E4 orf1 to orf4 genes, and also relates to the use thereof.

BACKGROUND ART

Liver cancer is one of the most common cancers in the world, and has the third-highest mortality rate among all the cancers because of its high fatality rate. Despite the understanding of diseases and a major advance in therapeutic options for the past two decades, it is known that liver cancer is difficult to treat because it does not easily respond to conventional drugs, and often recurs after treatment because of the potential of invasion and metastasis.

Liver cancer therapies that have been generally performed to date are largely divided into surgical therapies, including partial hepatic resection or liver transplantation, and non-surgical therapies, including transcatheter arterial chemoembolization, percutaneous ethanol injection therapy, radiofrequency ablation and the like. However, such therapies are not easy to apply, because most liver cancer patients have deteriorated liver function due to the cirrhosis accompanying liver cancer. It is known that hepatic resection can be applied only about 10-20% of total liver cancer patients and also shows an annual recurrence rate of about 10-30%. Liver transplantation is not used as a general therapeutic method due to the lack of donors, and local therapy is limitedly used for the treatment of a small-sized cancer found at an early stage. In addition, systemic chemotherapy or radiotherapy known as broad-spectrum anticancer therapy shows only partial effects. Thus, a new therapeutic strategy against liver cancer has been required, and various studies on immunotherapy, hormone therapy and gene therapy have recently been conducted.

Gene therapy is a method in which a genetic material such as DNA or RNA is administered into the human body to induce the expression of a therapeutic protein or inhibit the expression of a specific protein in order to prevent and treat chronic diseases such as inherited or acquired genetic defects, viral diseases, cancers or cardiovascular diseases. It enables a disease to be thoroughly treated by analyzing the cause of the disease at the genetic level, and thus is a method that makes it possible to overcome incurable diseases and is expected as an alternative to conventional medical methods. Adenovirus vectors for gene therapy, which are generally used, are constructed by deleting a series of genes essential for replication and introducing a Cytomegalovirus (CMV) or Rous Sarcoma Virus (RSV) promoter having high activity in order to induce the expression of a therapeutic protein with high efficiency in vivo.

In recent years, cancer cell-specific therapy has been attempted in an effort to reduce side effects that are caused because a number of target genes that can be used in gene therapy are also expressed in normal cells that undergo significant cell division. Transcriptional targeting for cancer gene therapy that uses a cancer- or tissue-specific promoter is based on the property of cancer cells that overexpress or activate many genes important in unregulated proliferation and cell survival.

Meanwhile, it was reported that the group I intron ribozyme from *Tetrahymena thermophila* can link two separate transcripts to each other by performing a trans-splicing reaction not only in vitro but also in bacteria and human cells (Been, M. and Cech, T. 1986, One binding site determines sequence specificity of Tetrahymena pre-rRNA self-splicing, trans-splicing, and RNA enzyme activity. Cell 47: 207-216; Sullenger, B. A. and Cech, T. R. 1994, Ribozyme-mediated repair of defective mRNA by targeted, trans-splicing. Nature 371: 619-622; Jones, J. T., Lee, S. W., and Sullenger, B. A. 1996, Tagging ribozyme reaction sites to follow trans-splicing in mammalian cells. Nat Med. 2: 643-648).

Thus, the group I intron-based trans-splicing ribozyme can target a disease-related gene transcript or a specific RNA, which is not expressed in normal cells and is expressed specifically in diseased cells, and then induce reprogramming so that either the RNA will be restored to normal RNA, or the gene transcript will be replaced with a new therapeutic gene transcript. Thus, the trans-splicing ribozyme can be a disease-specific and safe gene therapy technology. Specifically, because RNA replacement will occur only in the presence of a target gene transcript, a desired gene product will be made only at a proper time and in a proper space.

Particularly, because it is a method in which RNA that is expressed in cells is replaced with a desired gene product after it is targeted, the level of gene to be introduced can be controlled. In addition, the trans-splicing ribozyme can significantly increase therapeutic effects, because it can remove disease-specific RNA and induce the expression of a desired therapeutic gene product.

In addition, a ribozyme-based human telomerase reverse transcriptase (hTERT)-targeting strategy was reported as a new method of treating liver cancer, because telomerase reverse transcriptase is not found in normal liver tissue, but is found in 89.5% of hepatocellular carcinoma (Nagao K, Tomimatsu M, Endo H et al: Telomerase reverse trasncriptase mRNA expression and telomerase activity in hepatocellular carcinoma. J Gastrenterol 1999; 34; 83-87). Human telomerase reverse transcriptase (hTERT) is one of the most important enzymes that regulate the immortality and proliferation ability of cancer cells. Germ cells, hematopoietic cells and cancer cells, which replicate infinitely, have a telomerase activity of 80-90%, but normal cells around cancer cells have no telomerase activity (Bryan, T. M. and Cech, T. R. 1999, Telomerase and the maintenance of chromosome ends. Curr. Opin. Cell Biol. 11; 318-324). Based on such characteristics of telomerase, in recent years, there has been an active attempt to inhibit the proliferation of cancer cells by developing a telomerase inhibitor that is involved in cell growth (Bryan, T. M., Englezou, A., Gupta, J., Bacchetti, S., and Reddel, R. R. 1995, Telomere elongation in immortal human cells without detectable telomerase activity. Embo J. 14; 4240-4248; Artandi, S. E. and DePinho, R. A. 2000, Mice without telomerase: what can they teach us about human cancer Nat. Med. 6; 852-855).

Accordingly, the present inventors have conducted studies on a gene therapy method of treating liver cancer, and have developed a gene therapy method that uses a recombinant adenovirus comprising a tissue-specific promoter and a trans-splicing ribozyme targeting a cancer-specific gene. Particularly, the present inventors have found that a recombinant adenovirus, which includes a liver tissue-specific phosphoenolpyruvate carboxykinase (PEPCK) gene promoter, a trans-splicing ribozyme operably linked to the promoter and acting on a cancer-specific gene, a therapeutic gene or reporter gene linked to the 3' exon of the ribozyme, and a serotype 35 fiber knob and serotype 5 shaft, and lacks adenovirus E1, E3 and E4 orf1 to orf4 genes, has significantly high therapeutic efficiency and safety, thereby completing the present invention.

SUMMARY

An object of the present invention is to provide a recombinant adenovirus having increased in vivo safety, tissue specificity and anticancer activity, and the use thereof.

In order to accomplish the above object, the present invention provides a recombinant adenovirus including: a liver tissue-specific phosphoenolpyruvate carboxykinase (PEPCK) gene promoter; a trans-splicing ribozyme operably linked to the promoter and acting on a cancer-specific gene; a therapeutic gene or reporter gene linked to the 3' exon of the ribozyme; and a serotype 35 fiber knob and serotype 5 shaft, the recombinant adenovirus lacking adenovirus E1, E3 and E4 orf1 to orf4 genes.

The present invention may also provide a pharmaceutical composition for treating liver cancer, which contains the recombinant adenovirus of the present invention as an active ingredient.

The present invention may also provide a pharmaceutical composition for diagnosing liver cancer, which contains the recombinant adenovirus of the present invention as an active ingredient.

The present invention may also provide a method of providing information for diagnosing liver cancer, the method including the steps of:
1) introducing the recombinant adenovirus of the present invention into a cancer cell; and
2) detecting a reporter protein in the cancer cell of step 1).

DESCRIPTION OF DRAWINGS

FIG. 16 shows the inhibition of invasion of liver cancer cells and angiogenesis by Ad-PRT. Representative invaded cells were imaged (upper), and data for each group were expressed as mean±SEM (***$p<0.001$) (right). The number of invaded cells was counted in at least five fields in three independent experiments, and statistical significance was evaluated using t-test.

DETAILED DESCRIPTION

Figure 1:
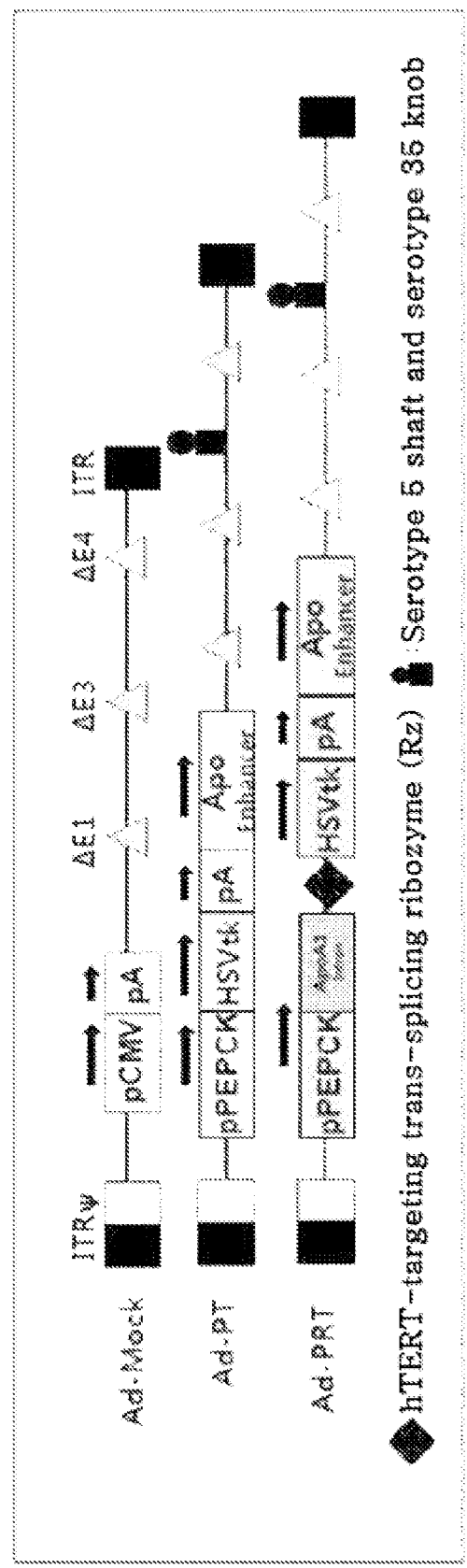
FIG. 1 is a schematic view of a recombinant virus according to the present invention.

Hereinafter, the terms used in the present invention will be described in detail.

The term "adenovirus" used herein has the same meaning as an adenovirus vector, and refers to a member of the family Adenoviridae. The Adenoviridae includes all animal adenoviruses of the genus Mastadenovirus. In particular, human adenoviruses include the A-F subgenera and the individual serotypes thereof. The A-F subgenera includes human adenovirus types 1, 2, 3, 4, 4a, 5, 6, 7, 8, 9, 10, 11 (Ad11A and Ad11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48 and 91.

The term "promoter" used herein refers to a nucleic acid sequence that controls the expression of an operably linked nucleic acid in a particular host cell, and the term "operably linked" means that one nucleic acid fragment is functionally bound to another nucleic acid fragment so that the function or expression of the one nucleic acid fragment will be influenced by the another nucleic acid fragment.

The term "tissue-specific promoter" used herein refers to an untranslated nucleic acid sequence located upstream of the coding region and having the activity of initiating the transcription of a gene downstream of the promoter into mRNA in a tissue-specific manner.

Hereinafter, the present invention will be described in detail.

The present invention provides a recombinant adenovirus including: a liver tissue-specific phosphoenolpyruvate carboxykinase (PEPCK) gene promoter; a trans-splicing ribozyme operably linked to the promoter and acting on a cancer-specific gene; a therapeutic gene or reporter gene linked to the 3' exon of the ribozyme; and a serotype 35 fiber knob and serotype 5 shaft, the recombinant adenovirus lacking adenovirus E1, E3 and E4 orf1 to orf4 genes.

The liver tissue-specific PEPCK gene promoter preferably has a nucleotide sequence set forth in SEQ ID NO: 1, but is not limited thereto.

The ribozyme is expressed only in a specific target tissue by the liver tissue-specific promoter. Through the action of the trans-splicing ribozyme having an ability to replace a cancer-specific gene with RNA, the ribozyme can exhibit trans-splicing activity in cancer tissue other than normal tissue, and thus the adenovirus does not act in tissue other than cancer tissue, suggesting that the side effects of gene therapy employing the adenovirus can be significantly reduced.

The promoter preferably further includes an ApoA1 intron having a nucleotide sequence set forth in SEQ ID NO: 2, but is not limited thereto.

The trans-splicing ribozyme acting on a cancer-specific gene is expressed only in a particular tissue by the tissue-specific promoter, and the ribozyme expressed only in the particular tissue targets a particular cancer-specific gene, which is expressed in cells, and performs a trans-splicing reaction to link a therapeutic gene or a reporter gene to the cancer-specific gene.

The term "cancer-specific gene" used herein refers to a gene that is expressed specifically in cancer cells. The cancer-specific gene is preferably hTERT (human telomerase reverse transcriptase) mRNA, AFP (alphafetoprotein) mRNA, CEA (carcinoembryonic antigen) mRNA, PSA (prostatespecific antigen) mRNA, or CKAP2 (cytoskeleton-associated protein 2) mRNA, but is not limited thereto.

The ribozyme is preferably a ribozyme that can target a cancer-specific gene and perform a trans-splicing reaction to link a new therapeutic gene or reporter gene to the cancer-specific gene. More preferably, the ribozyme is a hTERT-targeting trans-splicing group I ribozyme confirmed to have an ability to recognize and trans-splice the mRNA of hTERT that is a cancer-specific RNA transcript, but is not limited thereto.

The serotype 35 fiber knob and serotype 5 shaft is constructed by replacing a serotype 5 fiber knob region with a serotype 35 fiber knob region using a known method (Shayakhmetov D M, et. al. J Virol. 2000 November; 74(22):10274-86), but are not limited thereto.

The recombinant adenovirus preferably further include an ApoE (apolipoprotein E) gene enhancer (SEQ ID NO: 6), a PEPCK (phosphoenolpyruvate carboxykinase) gene enhancer, a serum albumin gene enhancer, an AFP (alphafetoprotein) gene enhancer, a CEA (carcinoembryonic antigen) gene enhancer or a PSA (prostate-specific antigen) gene enhancer, but is not limited thereto.

The recombinant adenovirus preferably lacks E4 orf1 to orf4 genes, but is not limited thereto. Further, the recombinant adenovirus lacking E4 orf1 to orf4 genes may be constructed by a known method (Yeh P, Dedieu J F, et. al. J Virol. 1996 January; 70(1):559-65), but is not limited thereto.

The E4 orf1 to orf4 genes damage normal cells, and thus if the recombinant adenovirus lacks the E4 orf1 to orf4 genes, the safety thereof will significantly increase. In addition, the recombinant adenovirus lacking the E4 orf1 to orf4 genes has an increased space for receiving an exogenous therapeutic gene, and thus can receive an exogenous therapeutic gene having a size of about 7 kb.

The therapeutic gene is preferably any one selected from the group consisting of drug-sensitizing genes, proapoptotic genes, cytostatic genes, cytotoxic genes, tumor suppressor genes, antigenic genes, cytokine genes and anti-angiogenic genes, and more preferably a HSV-tk (Herpes simplex virus-thymidine kinase) gene having a nucleotide sequence set forth in SEQ ID NO: 4, but is not limited thereto.

The term "drug-sensitizing gene" used herein refers to an enzymatic gene that converts a nontoxic prodrug into a toxic form. It is also referred to as a suicide gene, because cells transfected with the gene die. That is, when a prodrug that is non-toxic in normal cells is systemically administered, it is converted into toxic metabolites only in cancer cells by the drug-sensitizing gene to change drug sensitivity to thereby kill the cancer cells. Typical examples of a drug-sensitizing gene that may be used in the present invention include, but are not limited to, a HSV-tk (herpes simplex virus-thymidine kinase) gene, ganciclovir, an E. coli cytosine deaminase (CD) gene, 5-fluorocytosine (5-FC), etc.

The term "proapoptotic gene" used herein refers to a nucleotide sequence that is expressed to induce programmed cell death. Examples of the proapoptotic gene include p53, adenovirus E3-11.6K (derived from Ad2 and Ad5) or adenovirus E3-10.5K (derived from Ad), adenovirus E4 gene, p53 pathway gene, and caspase-coding gene.

The term "cytostatic gene" used herein refers to a nucleotide sequence that is expressed in cells to stop the cell cycle.

Typical examples of the cytostatic gene include p21, retinoblastoma gene, E2F-Rb fusion protein gene, cyclin-dependent kinase inhibitor-encoding genes (e.g., p16, p15, p18 and p19), growth arrest specific homeobox (GAX) genes (Internal Patent Publication Nos. WO 97/16459 and WO 96/30385), and the like.

The term "cytotoxic gene" used herein refers to a nucleotide sequence that is expressed in cells to exhibit a toxic effect. Examples of the cytotoxic gene include nucleotide sequences that encode Pseudomoas exotoxin, lysine toxin, diphtheriae toxin and the like. The term "tumor suppressor gene" used herein refers to a nucleotide sequence that can be expressed in target cells to inhibit tumor phenotypes or induce cell death. Typical examples of a tumor suppressor gene include tumor necrosis factor-α (TNF-α), p53 gene, APC gene, DPC-4/Smad4 gene, BRCA-1 gene, BRCA-2 gene, WT-1 gene, retinoblastoma gene (Lee et al., Nature, 329, 642, 1987), MMAC-1 gene, adenomatous polyposis coil protein (U.S. Pat. No. 5,783,666 to Albertsen et al.), deleted colorectal carcinoma (DCC) gene, MMSC-2 gene, NF-1 gene, ENT tumor suppressor gene located in chromosome 3p21.3 (Cheng et al. Proc. Nat. Acad. Sci., 95, 3042-3047, 1998), MTS1 gene, CDK4 gene, NF-1 gene, NF-2 gene and VHL gene.

The term "antigenic gene" used herein refers to a nucleotide sequence which is expressed in target cells to produce a cell surface antigenic protein that can be recognized in the immune system. Examples of an antigenic gene known to those skilled in the art include carcinoembryonic antigen (CEA) and p53 (Levine, A., International Patent Publication No. WO 94/02167).

The term "cytokine gene" used herein refers to a nucleotide sequence which is expressed in cells to produce cytokine. Typical examples of the cytokine gene include GM-CSF, interleukins (IL-1, IL-2, IL-4, IL-12, IL-10, IL-19 and IL-20), interferon α, β and γ (interferon α-2b), and fusions such as interferon α-2α-1.

The term "anti-angiogenic gene" used herein refers to a nucleotide sequence which is expressed in cells to release anti-angiogenic factors out of the cells. Examples of the anti-angiogenic gene include angiostatin, inhibitors of vascular endothelial growth factor (VEGF), endostatin, and the like. The PEPCK_APO intron-ribozyme_HSVtk sequence of the present invention has a nucleotide sequence set forth in SEQ ID NO: 24, but is not limited thereto.

In the present invention, a reporter gene can be spliced to a cancer-specific gene by the activity of the ribozyme. The reporter gene joined to the cancer-specific gene in a particular tissue is expressed as a reporter protein according to the transcriptional activity of the promoter. By measuring the activity or level of the expressed reporter protein, cancer cells can be diagnosed. Herein, the reporter gene may be one known in the field to which the present invention pertains. Preferably, the reporter gene is a gene that encodes LacZ, chloramphenicol acetyl transferase (CAT), Renila luciferase, firefly luciferase, red fluorescent protein (RFP), green fluorescent protein (GFP), secreted placental alkaline phosphatase (SEAP) or HSV-tk (Herpes simplex virus-thymidine kinase).

The activities of such reporter proteins can be measured using the following methods known to those skilled in the art: firefly luciferase (see de Wet J. et al., Mol. Cell Biol., 7, 725-737, 1987), Renila luciferase (see Lorenz W. W. et al., PNAS 88, 4438-42, 1991), chloramphenicol acetyl transferase (see Gorman C. et al., Mol. Cell Biol., 2, 1044-1051, 1982), LacZ (see Hall C. V. et al., J. Mol. Appl. Genet., 2, 101-109, 1983), human growth hormone (see Selden R. et al., Mol. Cell Biol., 6, 3173-3179, 1986), green fluorescent protein (see Chalfie M. et al., Science, 263, 802-805, 1994), and secreted placental alkaline phosphatase (see Berger, J. et al., Gene, 66, 1-10, 1988). In addition, when thymidine kinase is used as the reporter protein, the activity thereof can be measured using the PET (positron emission tomography) imaging method.

In an example of the present invention, the present inventors constructed a recombinant adenovirus which includes a liver tissue-specific phosphoenolpyruvate carboxykinase (PEPCK) gene promoter, a trans-splicing ribozyme operably linked to the promoter and acting on a cancer-specific gene, a therapeutic gene or reporter gene linked to the 3' exon of the ribozyme, and a serotype 35 fiber knob and serotype 5 shaft, and which lacks adenovirus E1, E3 and E4 orf1 to orf4 genes (see FIG. 1).

In addition, in order to examine the effect of a therapeutic gene in the presence or absence of an enhancer, a pPT-O recombinant adenovirus including no enhancer, and a pPT-O recombinant adenovirus including an enhancer were constructed and transfected into each of the Hep3B liver cancer cell line and the SK-OV3 ovarian cancer cell line, and then the uptake of GCV was analyzed. As a result, it was shown that the pPT-O recombinant adenovirus including no ApoE enhancer caused no significant change in the liver cancer cell line and the ovarian cancer cell line, whereas the pPT-O recombinant adenovirus including the ApoE enhancer showed significant HSVtk activity in the PEPCK-positive liver cancer cell line, but caused no significant change in the SK-OV3 ovarian cancer cell line (see FIG. 3).

Figure 4:
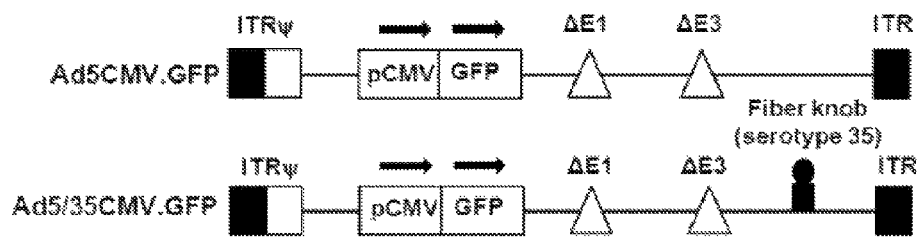
FIG. 4 is a schematic view showing a recombinant adenovirus (Ad5CMV.GFP), which comprises a CMV promoter and a green fluorescent protein (GFP) and lacks E1 and E3 genes, and a recombinant adenovirus (Ad5/35CMV.GFP) which comprises a CMV promoter, a green fluorescent protein (GFC) and a serotype 35 fiber knob and serotype 5 shaft and lacks E1 and E3 genes.

In addition, in order to analyze the infectivity of an adenovirus including a serotype 35 fiber knob and serotype 5 shaft, the recombinant adenoviruses shown in FIG. 4 were constructed, and the number of adenoviral genomes in the Hep3B liver cancer cell line was measured by quantitative PCR. As a result, it was shown that the infectivity of Ad5/35CMV.GFP including the serotype 35 fiber knob and the serotype 5 shaft according to the present invention significantly increased compared to that of Ad5CMV.GFP (see FIGS. 5 and 6).

In addition, in order to analyze the liver cancer-specific anticancer effect of the recombinant adenovirus Ad-PRT of the present invention, the recombinant adenovirus was infected into each of the Hep3B liver cancer cell line and the SK-OV3 ovarian cancer cell line, and then the cells were treated with GCV, and the percent survival of the cells was measured. As a result, it was shown that the recombinant adenovirus of the present invention did not show significant cell death in the ovarian cancer cell line, suggesting that it is liver cancer-specific (see FIG. 7).

Moreover, in order to analyze the trans-splicing activity of the recombinant adenovirus Ad-PRT of the present invention, the recombinant adenovirus was infected into each of the Hep3B liver cancer cell line and the SK-OV3 ovarian cancer cell line, and then RNA from the cells was analyzed. As a result, it was shown that the recombinant adenovirus of the present invention produced trans-spliced molecules (TSM) in the liver cancer cell line (see FIG. 8).

In addition, in order to analyze the liver cancer-specific toxic effect of the recombinant adenovirus Ad-PRT of the present invention, the apoptotic effect of the recombinant adenovirus was analyzed using a liver cancer cell line, a non-liver cancer cell line, a lung cancer cell line and a colorectal cancer cell line. As a result, it was shown that the recombinant adenovirus of the present invention showed a significant apoptotic effect only in the liver cancer cell line (see FIG. 9).

In addition, in order to analyze the in vivo liver cancer-specific targeting ability of the recombinant adenovirus Ad-PRT of the present invention, the recombinant adenovirus was administered to mice, and the detection of contrast medium was performed by micro-PET/CT. As a result, it was shown that the contrast medium was extensively detected in a positive control group, but no contrast medium absorption signal appeared in the recombinant adenovirus, suggesting that the recombinant adenovirus of the present invention shows high specificity for gene target tissue (see FIG. 10). Further, in order to examine whether the recombinant adenovirus Ad-PRT of the present invention was properly infected in a liver cancer-specific manner, RNA was isolated from each of a normal region and a liver cancer region and analyzed by RT-PCR. As a result, it was shown that the recombinant adenovirus terminal region (ITR) of the present invention and a therapeutic gene (TK) were significantly expressed in liver cancer tissue (see FIG. 12).

In addition, in order to analyze the in vivo safety of the recombinant adenovirus of the present invention, the survival plot, liver function evaluation and TUNEL analysis of mice treated with the recombinant adenovirus were performed. As a result, it was shown that the mice administered with the recombinant adenovirus of the present invention all survived, and no reduction in liver function appeared, and normal liver cells were not pathologically affected, suggesting that the recombinant adenovirus of the present invention shows significant safety (see FIGS. 13 to 15).

In addition, the effect of hTERT removal on tumor cell invasion was analyzed using a Matrigel invasion assay and an immunohistochemical assay. As a result, it was shown that the ribozyme-mediated removal of hTERT showed anticancer activity in vivo by suppressing cancer metastasis- or angiogenesis-related pathways (see FIGS. 16 and 17).

Furthermore, in order to analyze the in vivo anticancer effect of the recombinant adenovirus Ad-PRT of the present invention, the micro-PET/CT imaging, tissue analysis and tumor weight analysis of mice treated with the recombinant adenovirus were performed. As a result, it was shown that the recombinant adenovirus Ad-PRT of the present invention exhibited strong activity against liver cancer (see FIGS. 18 to 24).

Accordingly, the recombinant adenovirus according to the present invention has enhanced in vivo safety, high specificity for target tissue and a significant anticancer effect, and thus can be effectively used as an anticancer pharmaceutical composition in gene therapy.

The present invention also provides a pharmaceutical composition for treating liver cancer, which contains the recombinant adenovirus of the present invention as an active ingredient.

For administration, the anticancer pharmaceutical composition of the present invention may preferably be formulated to contain at least one pharmaceutically acceptable carrier in addition to the active ingredient as described above.

When the composition of the present invention is formulated in a liquid form, the pharmaceutically acceptable carrier that is contained in the composition of the present invention at least one selected from among physiological saline, sterile water, Ringer's solution, buffered saline, albumin injection solution, dextrose solution, maltodextrin solution, glycerol, and ethanol, which are sterile and biocompatible. If necessary, other conventional additives, including an antioxidant, a buffer and a bacteriostatic agent, may be added to the composition. In addition, the pharmaceutical composition may be formulated in injectable dosage forms such as an aqueous solution, a suspension or an emulsion, pills, capsules, granules, or tablets by adding a diluent, a dispersing agent, a surfactant, a binder and a lubricant. In addition, a target organ-specific antibody or ligand bound to the carrier may be used so that the composition can act specifically in a target organ.

Because the recombinant adenovirus that is contained in the composition of the present invention exhibits antitumor effects against various tumor cells, the pharmaceutical composition of the present invention may be used for the treatment of various tumor-related diseases, for example, brain cancer, gastric cancer, lung cancer, breast cancer, ovarian cancer, liver cancer, bronchial cancer, nasopharyngeal cancer, laryngeal cancer, esophageal cancer, pancreatic cancer, bladder cancer, prostate cancer, colorectal cancer, colon cancer, bone cancer, skin cancer, thyroid cancer, parathyroid cancer, ureteral cancer, and cervical cancer.

The pharmaceutical composition of the present invention is preferably administered parenterally, for example, intravenously, intraperitoneally, intratumorally, intramuscularly, subcutaneously or topically, but is not limited thereto. For example, if the composition is to be administered intraperitoneally in ovarian cancer or administered into portal veins in liver cancer, it may be administered by injection. In addition, in the case of breast cancer and head and neck cancer, the composition may be administered by direct injection into a tumor mass, and in the case of colon cancer, it can be administered by direct injection into the rectum, and in the case of bladder cancer, it may administered by direct inject into the catheter.

The dose of the anticancer pharmaceutical composition of the present invention can be determined depending on the kind and severity of the disease, the kind and content of active ingredient and other components in the composition, the kind of formulation, the patient's age, weight, general health condition, sex and diet, the time of administration, the route of administration, the excretion rate of the composition, the duration of treatment, and drugs used in combination with the composition.

However, for preferred effects, the pharmaceutical composition of the present invention generally contains $1\times10^5$ to $1\times10^{15}$ PFU of the recombinant adenovirus, and is generally injected at a dose of $1\times10^{10}$ PFU once two days for 5 days. The pharmaceutical composition of the present invention may be used alone or in combination with therapy such as surgery.

Chemotherapeutic agents that may be used in combination with the composition of the present invention include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. Radiotherapies that may be used in combination with the composition of the present invention include X-ray radiation and gamma-ray radiation. Preferably, the composition of the present invention is used in combination with ganciclovir.

The present invention also provides a composition for diagnosing liver cancer, which contains the recombinant adenovirus as an active ingredient.

The present invention also provides a method of providing information for diagnosis of liver cancer, which includes the steps of: 1) introducing the recombinant adenovirus into a cancer cell; and 2) detecting a reporter protein in the cancer cell.

Because the recombinant adenovirus of the present invention enables host cells to express a reporter protein, cancer cells the recombinant adenovirus introduced therein can express a reporter protein. Detection of this reporter protein can be performed using any method known in the art.

Cancer or tumor that can be diagnosed by the method of the present invention is not specifically limited, and is preferably gastric cancer, lung cancer, breast cancer, ovarian cancer, liver cancer, bronchial cancer, nasopharyngeal cancer, laryngeal cancer, pancreatic cancer, bladder cancer, colorectal cancer, colon cancer, cervical cancer, brain cancer, prostate cancer, bone cancer, skin cancer, thyroid cancer, parathyroid cancer or ureteral cancer. It is most preferably liver cancer.

Hereinafter, the present invention will be described in further detail with reference to examples and experimental examples. It is to be understood, however, that these examples and experimental examples are for illustrative purposes only and are not intended to limit the scope of the present invention.

MODE FOR INVENTION

Example 1: Construction of Recombinant Adenovirus

To construct the recombinant adenovirus of the present invention, a ribozyme was constructed according to the method described in the literature (Kwon et al., Mol. Ther. 12: 824-834, 2005). Also, the PEPCK gene promoter was constructed according to the method described in the literature (Kwon, B. S. et al, FEBS Lett 580, 5033-5043, 2006). In addition, a pcDNA 3.1 (Invitrogen) vector (pPEPCK-.Rz.HSVtk) including PEPCK.Rz.HSVtk composed of the PEPCK promoter, an ApoA1 (Apolipoprotein A1) intron, the ribozyme and the HSVtk gene was constructed according to the method described in the literature (Song M S, et. al. Cancer Gene Ther2009; 16:113-125.). Next, PEPCK.HSVtk was cleaved from the pcDNA 3.1 (Invitrogen) vector including PEPCK.Rz.HSVtk by SalI and SmaI restriction enzymes, and was ligated with a pZAP1.1ΔNotI/BglII vector (OD260, Boise, Id.) previously cleaved by SalI and EcoRV restriction enzymes, thereby constructing pZAP1.1 (PEPCK.TK). In addition, BglII and NotI in the pZAP1.1ΔNotI/BglII vector were previously removed in order to avoid the overlapping of the restriction enzymes into which the ribozyme was to be introduced. Next, a ribozyme sequence that recognizes hTERT was amplified from a CMV-Ribo-TK vector (provided by professor Sung-Wook, Lee, Dankook University) using the following primers. The amplified ribozyme (treated with BamHI/HpaI) was ligated with the constructed pZAP1.1 (PEPCK-TK) vector (BglII NotI (treated by Klenow), thereby constructing pZAP1.1 (PEPCK.Rz/As.TK).

```
Primer:
                                         (SEQ ID NO: 7)
FW→ 5'-ACG TAT
    GGA TCC GTt TAG TGA ACC GTC AGA ATT
            BamHI
    GTT-3'

(SEQ ID NO: 8)
BW→ 5'-ACG TAT GTT AAC TTT CGA GTA CTC CAA AAC
                  HpaI
    TAA T-3'
```

Next, a poly A signal (SEQ ID NO: 5) and an enhancer (SEQ ID NO: 6) were linked to the constructed pZAP1.1 (PEPCK.Rz/As.TK) to construct a pZAP1.1 (PEPCK.Rz/As.TK) complete form. In addition, deletion adenovirus E1, E3 and E4 orf1 to orf4 genes was performed using a known method (Yeh P, Dedieu J F, et. al. J Virol. 1996 January; 70(1):559-65). Then, a fiber knob region in pAd363 (OD260) was replaced with a serotype 35 fiber knob by a known method (Shayakhmetov D M, et. al. J Virol. 2000 November; 74(22):10274-86) to construct pAd363.35fk, which was then ligated to the constructed pZAP1.1 (PEPCK.Rz/As.TK) complete form that had been cleaved with SfiI, thereby constructing a recombinant adenovirus vector. The constructed vector was amplified in HEK293 cells (FIG. 1).

Example 2: Cell Culture

The human cancer cell lines and human mammary epithelial cell line (HMEC) used in the present invention were all purchased from ATCC (American Type Culture Collection).

Hep3B cells and HMECs were cultured in RPMI1640 media containing 10% fetal bovine serum (FBS) (Invitrogen, USA) and 1% penicillin/streptomycin (P/S) (Invitrogen, USA). The cell lines were all used in the following experiments after they were cultured in an incubator under the conditions of 37° C. and 5% carbon dioxide.

Figure 2:
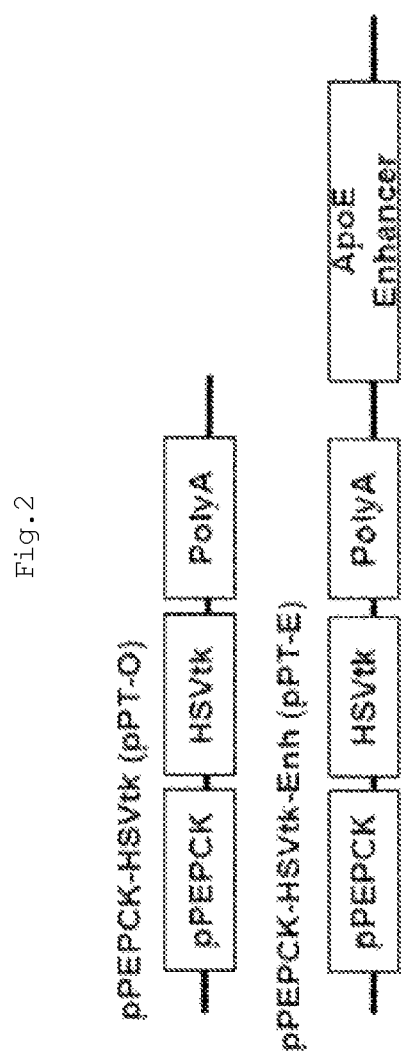
FIG. 2 is a schematic view showing a pPEPCK-HSVtk (pPT-O) adenovirus comprising a tissue-specific PEPCK (phosphoenolpyruvate carboxykinase) promoter and HSVtk (Herpes simplex virus-thymidine kinase), and a pPEPCK-HSVtk-Enh (pPT-E) recombinant adenovirus comprising PEPCK, HSVtk and an ApoE (Apolipoprotein E) enhancer.

Experimental Example 1: Analysis of Effect of Therapeutic Gene in the Presence or Absence of Enhancer In order to analyze the PEPCK-induced activity of PEPCK in the presence or absence of an ApoE enhancer, a pPEPCK-HSVtk (pPT-O) recombinant adenovirus comprising the tissue-specific promoter PEPCK and HSVtk, and a pPEPCK-HSVtk-Enh (pPT-E) recombinant adenovirus comprising PEPCK, HSVtk and an ApoE enhancer, were constructed in the same manner as described in Example 1 (FIG. 2). Then, 1 MOI of each of the recombinant adenoviruses was infected into each of the Hep3B liver cancer cell line and the SK-OV3 ovarian cancer cell line in 24-well plates. At 48 hours after infection, the infected cells were treated or not treated with 1.0 mCi/ml [8-$^3$H]penciclovir (PCV), and then incubated at 37° C. for 2 hours. Then, the cells were lysed in 200 ml of 0.1% SDS, and the radioactivity thereof was measured.

Figure 3:
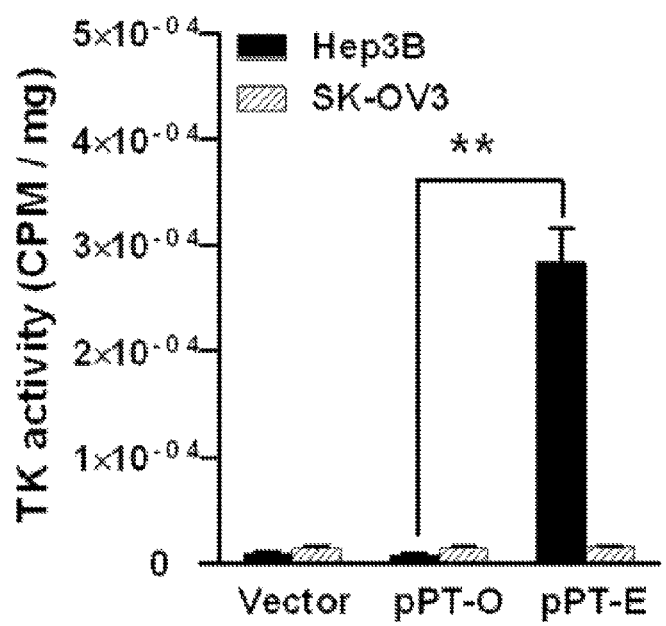
FIG. 3 shows the results of measuring the HSVtk activity induced by PEPCK in the presence of an ApoE enhancer.

As a result, as can be seen in FIG. 3, the pPT-O recombinant adenovirus including no ApoE enhancer caused no significant change in the liver cancer cell line and the ovarian cancer cell line, whereas the pPT-E recombinant adenovirus including the ApoE enhancer showed significant HSVtk activity in the PEPCK-positive liver cancer cell line, but caused no significant change in the SK-OV3 ovarian cancer cell line (FIG. 3).

Experimental Example 2: Analysis of Infectivity of Adenovirus including Serotype 35 Fiber Knob and Serotype 5 Shaft In order to analysis the infectivity of a recombinant adenovirus including a serotype 35 fiber knob and serotype 5 shaft, a recombinant adenovirus (Ad5CMV.GFP), which includes a CMV promoter and a green fluorescent protein (GFC) and lacks E1 and E3 genes, was constructed. In addition, a recombinant adenovirus (Ad5/35CMV.GFP), which includes a CMV promoter, a green fluorescent protein (GFC) and a serotype 35 fiber knob and serotype 5 shaft and lacks E1 and E3 genes, was constructed (FIG. 4). Each of the constructed recombinant adenoviruses was infected into the Hep3B liver cancer cell line, and then the number of GFP-positive cells was counted by flow cytometry and microscopic observation. In addition, the number of adenovirus genome copies in the Hep3B liver cancer cell line infected with each of Ad5CMV.GFP and Ad5/35CMV.GFP was measured by quantitative PCR.

Specifically, DNA was extracted using a QIAamp DNA mini kit and dissolved in 60 ul of nuclease-free water, and then the concentration of the DNA was measured by Nano-Drop. Quantitative PCR (qPCR) was performed using 50 ng of genomic DNA in a total volume of 20 ml comprising 10 ml 2×SYBR Premix Ex Taq (TaKaRa BIO INC, Japan), 200 nM target primer set (AdITR-F: 5'-AGC CAA TAT GAT AAT CAG GGG GTG-3' (SEQ ID NO: 9), and AdITR-R: 5'-TAC GCG CTA TGA GTA ACA CAA A-3' (SEQ ID NO: 10)) and 0.4 ml of 50×ROX reference dye. The PCR was performed using ABI PRISM 7900HT (Applied Biosystems, USA) for 40 cycles, each consisting of 30 sec at 95° C. and 1 min at 60° C.

Amplification of β-actin was performed with the gene of interest, and the relative level of expression of the target protein was analyzed by Ct defined as follows: —[$Ct_{target}Ct_{\beta-actin}$]. The standard curve was determined in the range of $10^1$ to $10^9$ adenovirus particles. In each analysis, a control including no template was used. All measurements were performed in triplicate. Samples with a coefficient of variation of 5% or higher were tested again.

Figure 5:
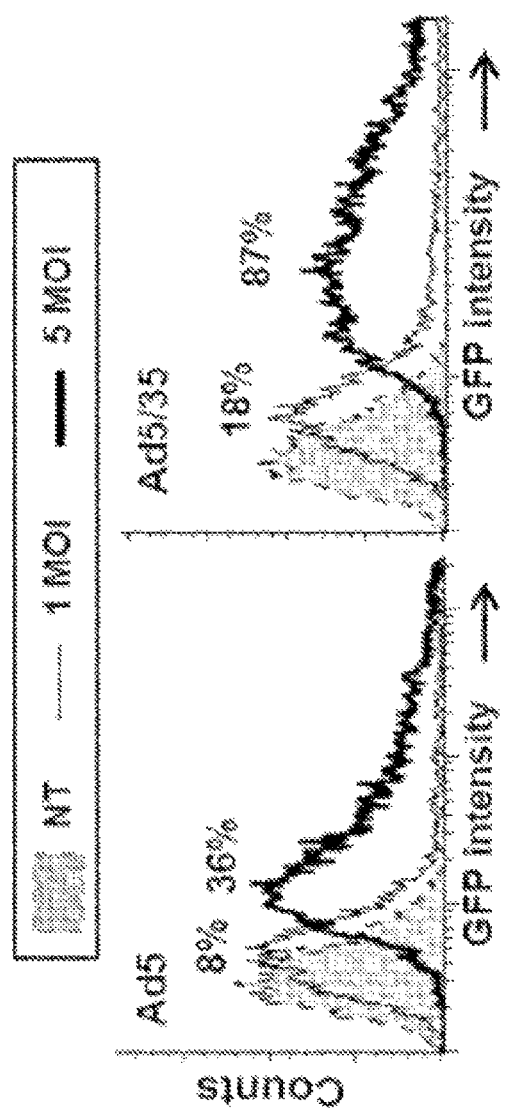
FIG. 5 shows the number of GFP-positive cells counted after a Hep3B liver cancer cell line infected with each of Ad5CMV.GFP and Ad5/35CMV.GFP.
Figure 6:
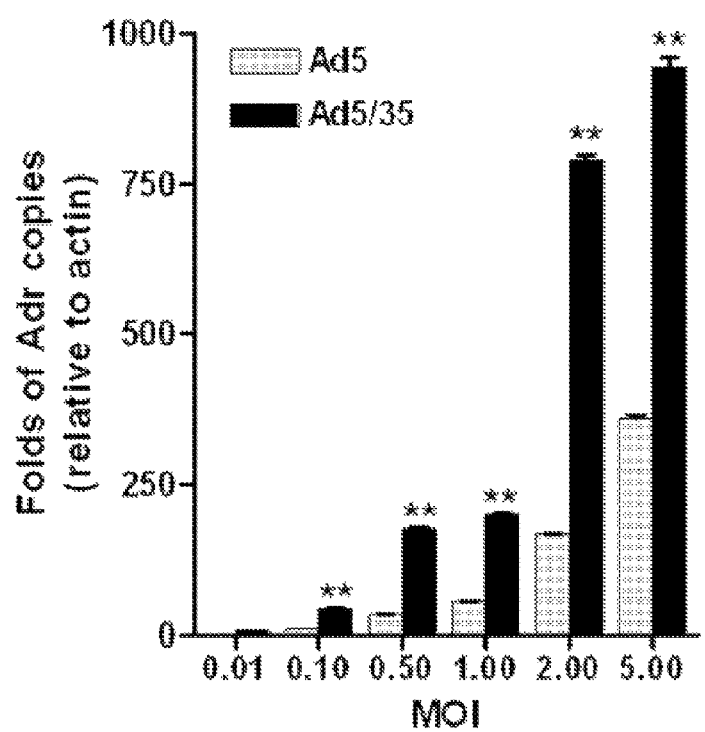
FIG. 6 shows the results of measuring the number of adenoviral genomes in an Ad5/35CMV.GFP-infected Hep3B liver cancer line by quantitative PCR.

As a result, as can be seen in FIGS. 5 and 6, the infectivity of the Ad5/35CMV.GFP including the serotype 35 fiber knob and serotype 5 shaft according to the present invention significantly increased compared to that of Ad5CMV.GFP (FIGS. 5 and 6).

Experimental Example 3: Analysis of Liver Cancer-Specific Effect of Recombinant Adenovirus In order to analyze the liver cancer-specific anticancer effect of a recombinant adenovirus including a liver tissue-specific PEPCK promoter, a hTERT (human telomerase reverse trasncriptase)-targeting ribozyme and a serotype 35 fiber knob and serotype 5 shaft, each of Ad-PRT, Ad-PT and Ad-Mock was infected into each of the Hep3B liver cancer cell line and the SK-OV3 ovarian cancer cell line at various MOI (multiplicities of infection), and then treated with 100 μm ganciclovir (GCV). At 5 days after ganciclovir treatment, crystal violet analysis was performed to measure the percent survival of the cells.

Specifically, crystal violet analysis was performed by removing the culture medium from each cell line, washing the cells twice with PBS, adding a 2.3% crystal violet solution to the cells, incubating the cells with the crystal violet solution, washing the incubated cells with PBS, and then fixing the cells with 100% MeOH.

Figure 7:
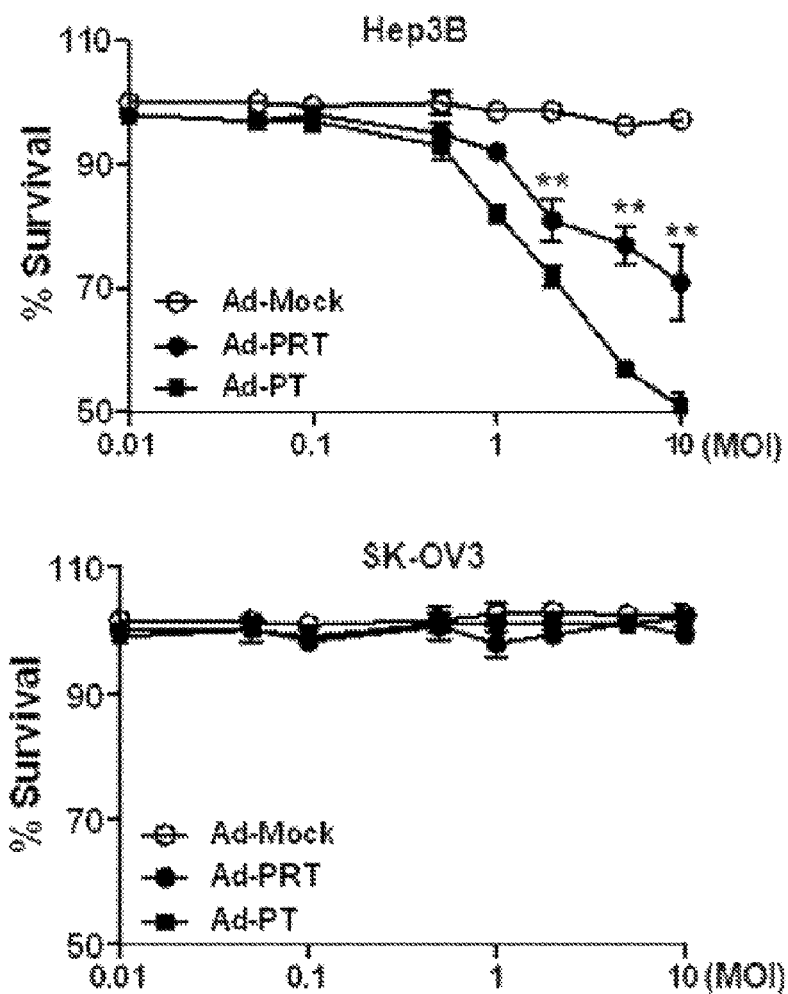
FIG. 7 shows the results of analyzing the liver cancer-specific effect of a recombinant adenovirus of the present invention.

As a result, as can be seen in FIG. 7, the death rate of the liver cancer cell line Hep3B was higher in the cells infected with each of Ad-PRT and Ad-PT than in the cells infected with Ad-Mock, and the ovarian cancer cell line SKOV3 showed no significant cell death in all Ad-PRT, Ad-PT and Ad-Mock, suggesting that Ad-PRT of the present invention is liver cancer-specific (FIG. 7).

Experimental Example 4: Analysis of Trans-Splicing Activity of Ad-PRT

In order to analyze the trans-splicing activity of Ad-PRT constructed in Example 1, each of Ad-PRT and Ad-Mock was infected into each of the Hep3B liver cancer cell line and the SK-OV3 ovarian cancer cell line at MOIs of 0, 1, 5 and 10, and then RNA from the cells was analyzed.

Specifically, in order to measure the level of ribozyme RNA of the cells treated with the recombinant adenovirus, total RNA was extracted from each cell line using a solution of Trizol (Invitrogen, Carlsbad, Calif.) containing 20 mM EDTA, and was then reverse-transcribed using 10 mM L-arginine amide and an oligo (dT) primer. Complementary DNA was amplified using HSVtk-specific primers (5'-GCGAACATCTACACCACACA-3' (SEQ ID NO: 11) and 5'-AGTTAGCCTCCCCCATCTC-3' (SEQ ID NO: 12)). In addition, for verification, complementary DNA was amplified using GAPDH-specific primers (5'-TGACATCAAGAAGGTGGTGA-3' (SEQ ID NO: 13) and 5'-TCCACCACCCTGTTGCTGTA-3' (SEQ ID NO: 14)). To detect trans-spliced RNA products in the cells, the total RNA was reverse-transcribed using a HSVtk-specific primer (5'-CGGGGATCCTCAGTTAGCCTCCCCCAT-3' (SEQ ID NO: 15)) in the presence of 10 mM L-arginine amide, and complementary DNA was amplified using the transcription product as a template together with a 5' primer (5'-GGGGAATTCAGCGCTGCGTCCTGCT-3' (SEQ ID NO: 16)) specific to the 5' end of hTERT RNA and a 3' primer (5'-GTTATCTGGGCGCTTGTCAA-3' (SEQ ID NO: 17)) specific to the 3' end of HSV-tk. Using the complementary DNA as a template, amplification with a 5' primer (5'-GCTGCGTCCTGCTAAAAC-3' (SEQ ID NO: 18)) specific to a trans-spliced region and a nested 3' primer (5'-CAGTAGCGTGGGCATTTTCT-3' (SEQ ID NO: 19)) specific to the nucleotide sequence of HSVtk was performed, and cloning and sequencing were also performed.

Figure 8:
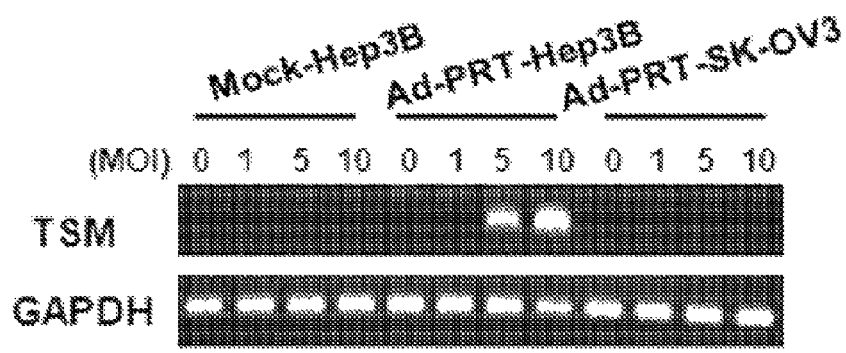
FIG. 8 shows the results of measuring the trans-splicing activity of Ad-PRT.

As a result, as can be seen in FIG. 8, trans-spliced molecules (TSMs) were produced in the hTERT+ Hep3B cells infected with the Ad-PRT recombinant adenovirus, but no TSM was produced in the hTERT-SKOV3 cells. Thus, it was found that the trans-spliced molecules (TSMs) in the Ad-PRT-infected Hep3B cells resulted from the liver-specific trans-splicing reaction of the target hTERT RNA (FIG. 8).

Experimental Example 5: Analysis of Liver Cancer-Specific Toxicity of Ad-PRT

In order to analyze the liver cancer-specific toxic effect of Ad-PRT, each of the PEPCK-positive and hTERT-positive liver cancer cell lines (HepG2, SNU398 and SNU739) cultured in Example 2, and PEPCK-negative and hTERT-negative non-liver cancer cell lines (human epithelial cell (HDF), lung cancer cell line (SBC-5) and colorectal cancer cell line (HCT116)), was treated with 10 MOI of Ad-PRT, and then the apoptotic effect of Ad-PRT was examined in the same manner as described in Experimental Example 3.

Figure 9:
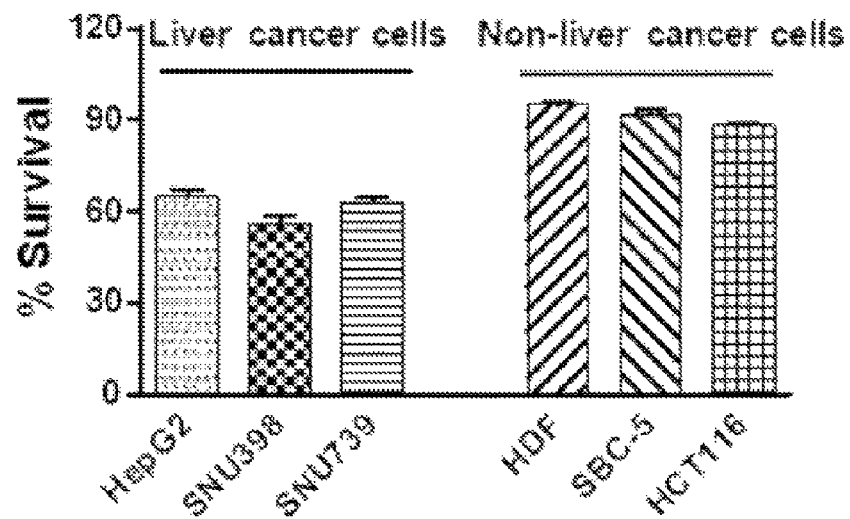
FIG. 9 shows the results of measuring liver cancer-specific effects in PEPCK-positive and hTERT-positive liver cancer cell lines (HepG2, SNU398 and SNU739), a PEPCK-negative and hTERT-negative non-liver cancer cell line (human epithelial cell; HDF), a lung cancer cell line (SBC-5) and a colorectal cancer cell line (HCT116).

As a result, as can be seen in FIG. 9, Ad-PRT caused no significant change in the non-liver cancer cell lines, but showed a significant apoptotic effect on the liver cancer cell line. Thus, it was found that Ad-PRT of the present invention exhibits a liver cancer-specific toxic effect (FIG. 9).

Experimental Example 6: Analysis of Liver Cancer-Specific Targeting Ability of Ad-PRT in Vivo 6-1: Experimental Animals As experimental animals, 4-5-week-old male Balb/c-nude mice (Orient Bio, Korea) were used. The experimental animals were kept under pathogen-free conditions, and acclimated to laboratory conditions for at least one week before use. Also, the animals were maintained in National Cancer Center animal facility in accordance with AAALAC International Animal Care policy (accredited unit-National Cancer Center Research Institute: unit number-1392).

6-2: Analysis of Liver Cancer-Specific Targeting Ability of Ad-PRT

In order to analyze the liver cancer-specific targeting ability of Ad-PRT in vivo, the recombinant adenovirus of the present invention was systemically administered to the mice of Experimental Example 6-1, which had not the recombinant virus of the present invention, and whether the normal liver was infected with the adenovirus was examined by micro-PET/CT using [$^{18}$F]FHBG (9-(4-[$^{18}$F]fluoro-3-hydroxymethylbutylguanine) contrast medium.

Specifically, when TK (thymidine kinase) was expressed by the recombinant adenovirus of the present invention in the liver infected with the recombinant adenovirus, [$^{18}$F] FHBG contrast medium was absorbed into the cells infected with the recombinant adenovirus, and was detected using micro-PET/CT. Specifically, 5×10$^8$ pfu of each of Ad-Mock, Ad-CT, Ad-PT and Ad-PRT constructed in Example 1 was systemically injected into non-cancer-induced mice through the tail vein, and at 2 days after injection, imaged by micro-PET/CT.

In addition, in order to detect the expression of HSVtk by PET, nude mice injected with each of Ad-Mock, Ad-CT, Ad-PT and Ad-PRT were anesthetized with 2% isoflurane in 100% oxygen, and fasted for at least 6 hours, after which $^{18}$F-FHBG (14.8 MBq) was injected through the tail vein in the anesthetized state. [$^{18}$F]FHBG (9-(4-[$^{18}$F]fluoro-3-hydroxymethylbutylguanine) was used to detect the expression of HSVtk by PET.

For PET-CT hybrid imaging, a three-dimensional data collection mode (GE, USA) was performed under X-ray conditions for CT (300 μA and 40 kV for 6 min; resolution=200; acquired projection number=360). Images were normalized to standardized uptake values (SUV) using the following equation 1:

$$SUV = \text{decay corrected mean tissue activity concentration (Bq/ml)/injected dose (Bq)} \times \text{body weight (g)} \quad \text{Equation 1}$$

All MRI images were acquired using a 7 T Biospec spectrometer (Bruker, Germany). A T2-weighted fast spin echo pulse sequence was recorded with the following settings:

Repetition time (TR)=2,500 ms; echo time (TE)=30 ms; 256*256 matrix; field of view (FOV)=3*3 cm; slice thickness=0.7 mm; and number of average=2; RARE factor=4.

For PET/MR hybrid imaging, MRI imaging was performed after PET-CT scanning using a general bed. PET-MR hybrid imaging was performed using OsiriX imaging software.

Figure 10:
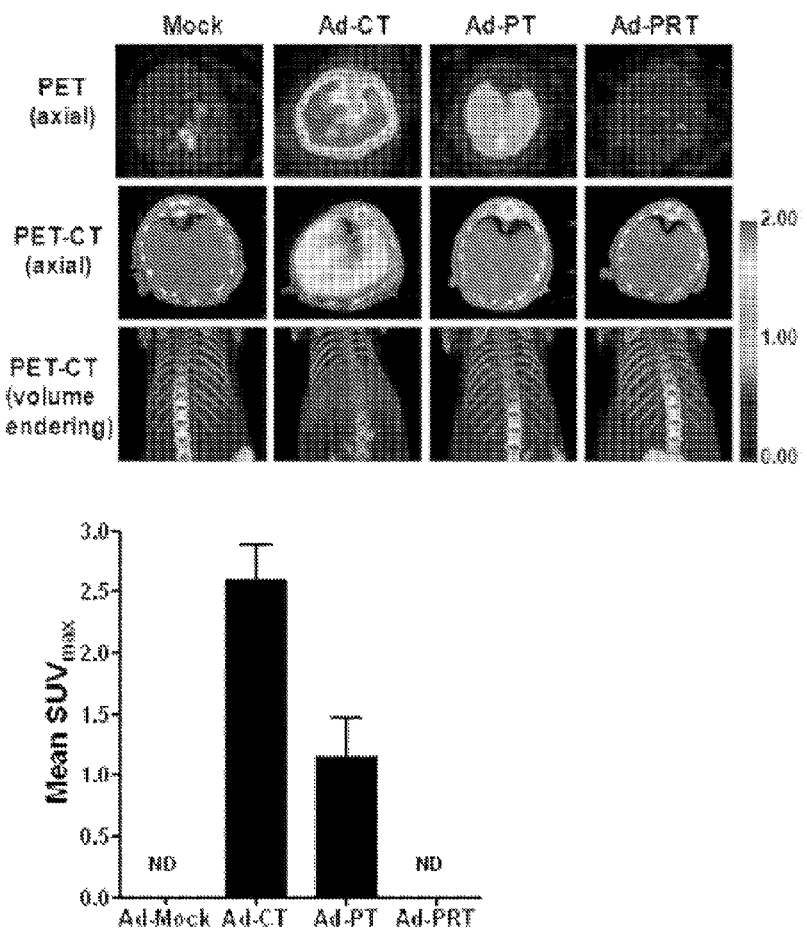
FIG. 10 depicts micro-PET/CT images and (standardized uptake values (SUV), which show the recombinant adenovirus-mediated expression of TK (thymidine kinase) gene in a normal liver.

As a result, as can be seen in FIG. 10, the [$^{18}$F]FHBG distribution associated with the HSVtk gene expression appeared extensively in the liver when each of Ad-PT and Ad-CT was administered, whereas, in the case of the Ad-PRT-administered group, a [$^{18}$F] FHBG absorption signal did not appear in the liver despite the strong inherent directionality of Ad-PRT toward the liver (FIG. 10). Thus, it was found that Ad-PRT of the present invention shows high specificity to gene target tissue through the dual regulation of the ribozyme and the tissue-specific PEPCK promoter.

Experimental Example 7: Analysis of Liver Cancer-Specific Targeting Ability of Ad-PRT in Cancer-Induced Mice In order to analyze the liver cancer-specific targeting ability of Ad-PRT in cancer-induced mice, each of Ad-PRT and Ad-Mock was systemically administered to mice, and whether the cancer cells were infected with the recombinant adenovirus was analyzed by micro-PET/MR using [$^{18}$F] FHBG contrast medium.

Specifically, the liver cancer cell line Hep3B was injected into mouse by intra-spleen injection, and after 3 weeks, 5×10$^8$ pfu of each of Ad-PRT and Ad-Mock was systemically injected into the mice through the tail veins, and the expression of HSVtk was analyzed by micro-PET/MR hybrid imaging. In addition, in order to examine the growth of liver cancer cells, PET imaging was performed using $^{18}$F-FDG (14.8 MBq), and MRI imaging was performed by PET-CT scanning, and PET/MR hybrid imaging was performed using OsiriX imaging software.

Further, in order to examine whether the cells were infected with the recombinant adenovirus of the present invention, RNA was isolated from each of the normal region (N) and tumor region (T) of the mice and analyzed by RT-PCR.

Specifically, the production of TSMs by Ad-PRT was examined by nested RT-PCR. First-step PCR was performed using a 5' primer (5'-GGG GAA TTC AGC GCT GCG TCC TGC T-3' (SEQ ID NO: 20)) for a trans-spliced region, and a 3' primer (5'-GTT ATC TGG GCG CTT GTC AA-3' (SEQ ID NO: 21)) for HSVtk. Second-step PCR was performed using a forward primer 5'-CGT CCT GCT AAA GTT GGC CGC-3' (SEQ ID NO: 22) for the internal sequence of HSVtk, and a reverse primer (5'-GCA GTTGCG TGG TGG TGG TT-3' (SEQ ID NO: 23)).

Figure 11:
FIG. 11 depicts microPET/MR fusion images showing the liver cancer-specific targeting ability of Ad-PRT in cancer-induced mice.
Figure 12:
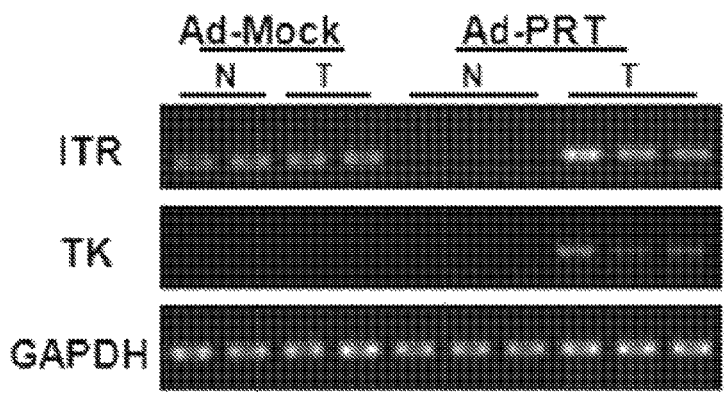
FIG. 12 shows the results of RT-PCR analysis of RNA isolated from each of a normal (N) region and a liver tumor (T) region, performed to examine whether the regions were infected with a recombinant adenovirus.

As a result, as can be seen in FIGS. 11 and 12, signals (white arrows) induced by Ad-PRT were detected in a tumor area caused by the liver cancer cell line, suggesting that the recombinant adenovirus of the present invention has a very high ability to target liver cancer (FIG. 11). In addition, it was shown that the adenovirus terminal region (ITR) and the therapeutic gene (TK) were significantly expressed in the Ad-PRT-infected liver cancer tissue (T) (FIG. 12).

Experimental Example 8: Analysis of in Vivo Safety of Ad-PRT 8-1: Preparation of Mouse Models for in Vivo Experiment and Administration of Virus Multiple liver cancer moue models mimicking human hepatocellular carcinoma (HCC) were prepared by administering 3×10$^6$ Hep3B cells to Balb/c-nude mice (Orient Bio, Korea) by intra-spleen injection. The animals were maintained in National Cancer Center animal facility in accordance with AAALAC International Animal Care policy (accredited unit-National Cancer Center Research Institute: unit number-1392).

In almost all the mice, multiple small tumor nodules that are easily detected by visual inspection were found in the liver, particularly at the boundary of the liver, 12 or days after administration of the Hep3B cells. In addition, tumor nodules were also found in the spleens of most of the mice.

8-2: Analysis of in Vivo Safety of Ad-PRT

In order to evaluate the safety of Ad-PRT, the tumor-bearing mice (n=10) prepared in the above section 8-1 were administered intravenously with 5×10$^8$ pfu of the adenovirus and treated with GCV for 14 days.

Specifically, the survival plot of the mouse group treated with each of Ad-Mock, Ad-CRT, Ad-PT and Ad-PRT was evaluated using the Kaplan-Meier method, and the liver function of the mice was measured by serum ALT and AST.

In addition, liver-specific enzyme levels (ALT and AST) were measured by a UV spectrophotometer at 3 and 6 days after GCV treatment, and histological observation of a number of representative cancer tissues (n=6/group) was performed by H&E staining. Further, the evaluation of cell death was performed using a TUNEL assay.

The TUNEL assay was performed using an in situ cell detection kit (Roche, Germany) in accordance with the manufacturer's instruction.

Figure 13:
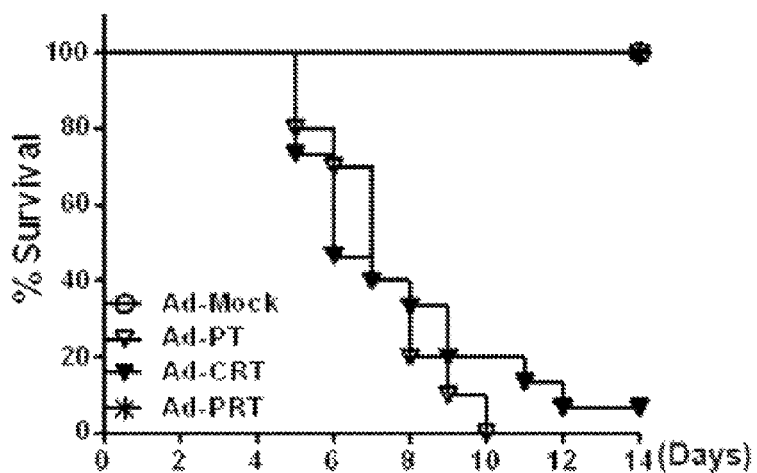
FIG. 13 shows the results of estimating the survival plots of mouse groups (n=10/group), treated with Ad-Mock, Ad-CRT, Ad-PT and Ad-PRT, using the Kaplan-Meier method.
Figure 14:
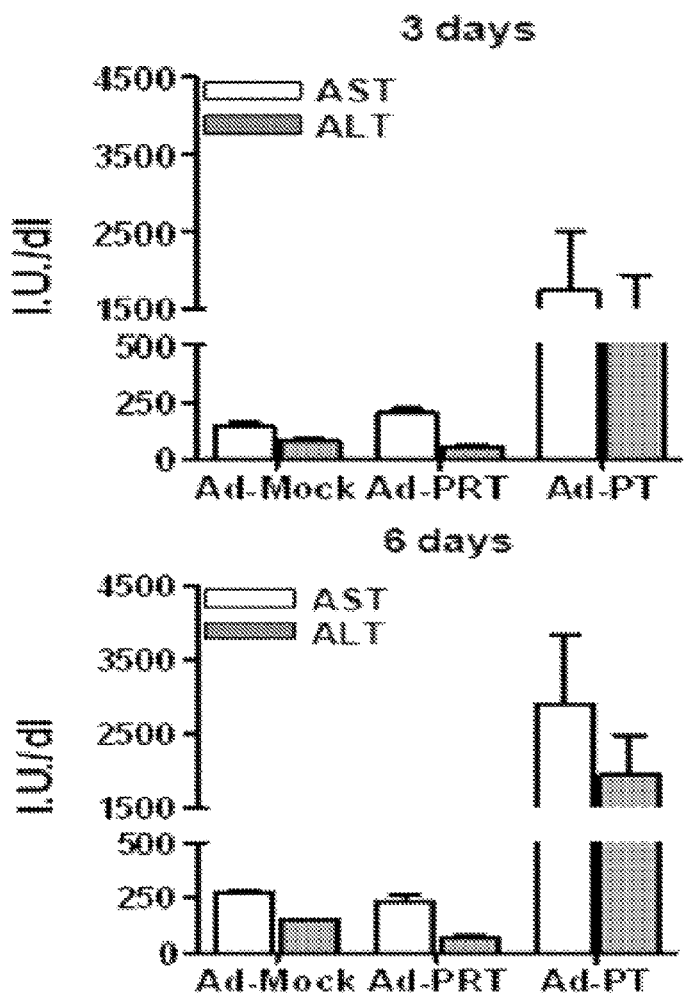
FIG. 14 shows the results of measuring the liver functions of Ad-Mock-, Ad-CRT-, Ad-PT- and Ad-PRT-treated mouse groups (n=10/group) using the liver-specific enzymes ALT and AST at 3 days and 6 days after GCV treatment. The error bar represents mean±SEM.

As a result, as can be seen in FIG. 13, the mice administered with Ad-PT survived up to about 10 days, whereas the mice administered with each of Ad-Mock and Ad-PRT all survived (FIG. 13). In addition, the levels of the liver-specific enzymes ALT and AST were very high in the Ad-PT group, but did not change in the Ad-PRT and Ad-Mock groups, and particularly, did not change even on 6 days (FIG. 14). Additionally, it was shown that Ad-CRT including the CMV promoter for regulating Rz-HSVtk in place of the PEPCK promoter showed strong toxicity similar to that of Ad-PT (FIG. 13).

Therefore, it was found that Ad-PRT of the present invention shows significantly high safety compared to Ad-PT and Ad-CRT.

Figure 15:
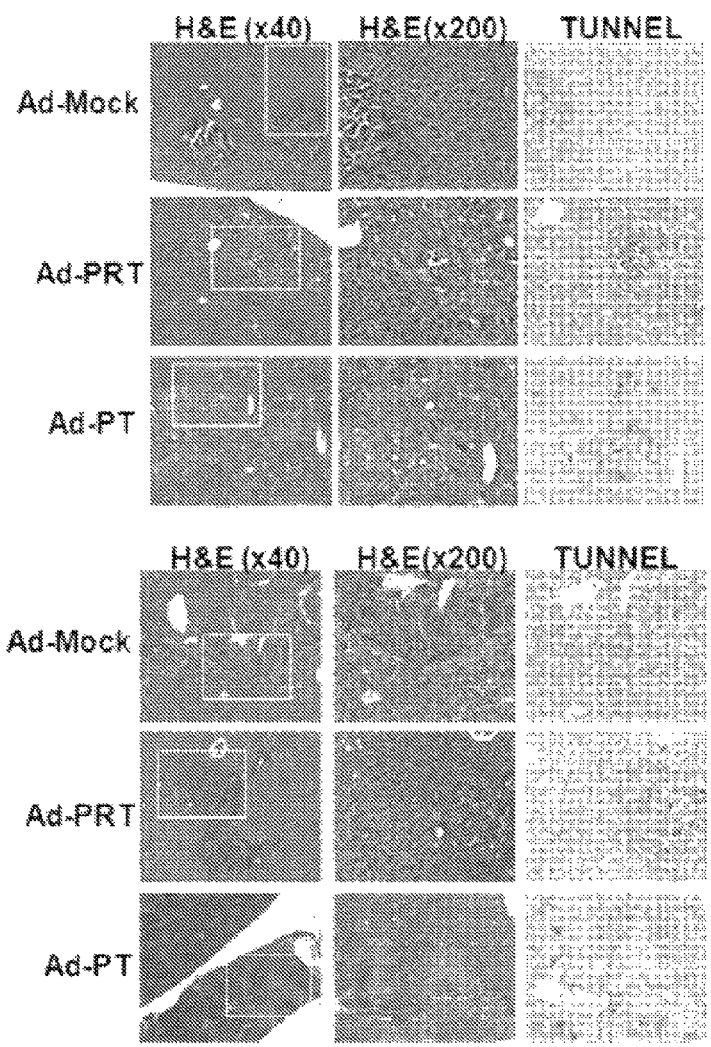
FIG. 15 shows the results of examining liver cancer tissue by H&E staining and the results of evaluating cell death by a TUNEL assay. Dark brown staining of the nucleus and the cell in the TUNEL assay indicates cell death.

In addition, as shown in FIG. 15, the results of histological examination performed by the present inventors revealed that normal liver cells in the Ad-PRT and Ad-Mock groups were not pathologically affected (FIG. 15). Specifically, the results of the TUNEL assay indicated that apoptotic features (e.g., dark brown spots) significantly appeared in the tumor nodules of the Ad-PRT-treated group. In contrast with this, in the Ad-PT-treated mice, the diffuse edema, spotty necrosis and death of liver cells appeared, and were more extensively enlarged on day 6 (FIG. 15). Apoptotic features were prominently observed in the tumor liver cells and non-tumor liver cells of the Ad-PT-treated group. The apoptotic frequency of tumor nodules in the Ad-PT-treated group was lower than that in the Ad-PRT-treated group. Such results suggest that introduction of the liver-specific PEPCK promoter provides additional safety in ribozyme-mediated targeting and that Ad-PRT can specifically target HCC without damaging non-tumor cells.

Experimental Example 9: Analysis of in Vivo Therapeutic Effect of Ad-PRT 9-1: Effect of hTERT Removal on Tumor Cell Invasion In order to analyze the effect of ribozyme-mediated hTERT removal on tumor cell invasion, a matrigel invasion assay was performed in adenovirus-treated cells not treated with GCV.

Specifically, at 4 days after viral infection, $5\times10^5$ Hep3B cells were plated on 24-well plates in the upper chambers of polycarbonate filters (6.5-mm diameter, 8.0 mm hole size, BD Bioscience, USA) coated with Matrigel (BD Bioscience, USA), and were cultured for 24 hours. Invaded cells were fixed and stained using a Diff-Quik staining kit (Sysmex, USA), and imaged and counted using a phase contrast microscope. Five randomly selected areas of each filter were quantified. In addition, immunohistochemical assays of liver samples embedded in 4- to 6-μm-thickness paraffin were performed using a semi-autoimmunostainer (Roche, Switzerland) in accordance with the manufacturer's instruction. The samples were treated with primary antibody (anti-VEGF-C; 1:50, anti-CD34; 1:200, AB Biotech), and immunostained using a 3,3'-diaminobenzidine substrate system. Slides were counter-stained blue with hematoxylin.

As a result, as can be seen in FIG. 16, strong inhibition of liver cancer cell invasion was observed in the Ad-PRT-infected group, unlike the untreated group or the Ad-MOCK-infected and Ad-PT-infected groups (FIG. 16).

Figure 17:
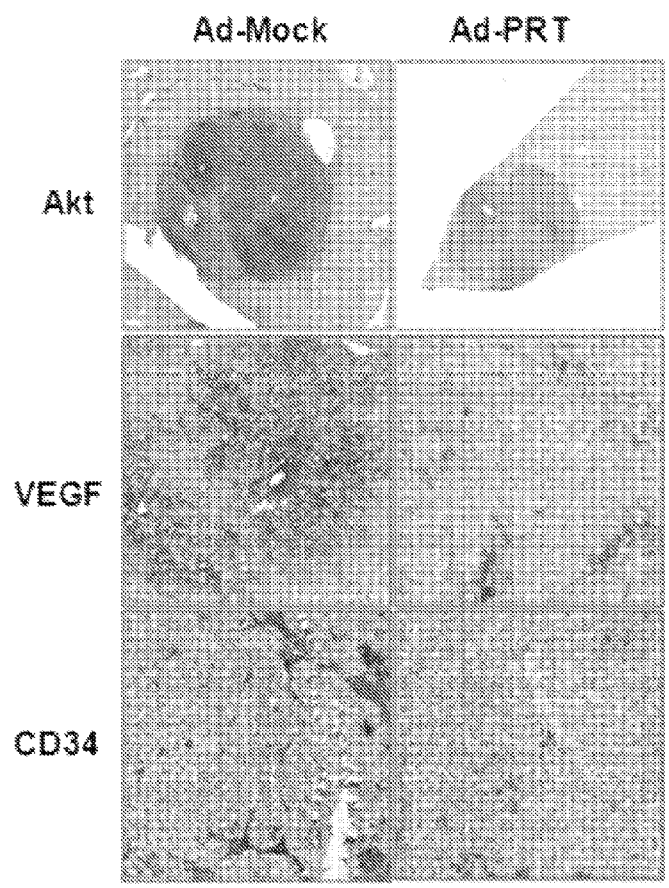
FIG. 17 shows an Ad-PRT-mediated decrease in the expression of VEGF and CD34 in mouse liver cancer cells, evaluated by immunohistochemical staining.

In addition, as shown in FIG. 17, liver cancer cells in the Ad-Mock-infected group were strongly stained with VEGF, but the expression of VEGF decreased rapidly in the Ad-PRT-infected group. Additionally, as shown in the CD34 immunostaining, angiogenesis in the tumor region was almost completely inhibited in the Ad-PRT-infected group compared to the Ad-Mock group (FIG. 17).

Thus, it was found that the ribozyme-mediated removal of hTERT exhibits anticancer activity in vivo by suppressing cancer metastasis- or angiogenesis-related pathways.

9-2: Analysis of Anti-HCC Effect of Ad-PRT in Liver Cancer in Hepatocellular Carcinoma Mouse Models In order to analyze the anti-HCC effect of Ad-PRT in hepatocellular carcinoma mouse models, 30 nude mice, randomly divided into an Ad-PRT group (20 mice) and an Ad-Mock group (10 mice), were administered with Hep3B cells. At 14 days after intravenous administration of Ad-PRT, the mice were monitored by in vivo imaging (n=10) and biopsy (n=30).

Specifically, to measure the anti-HCC effect, the mice were euthanized at 14 days after GCV treatment, and all the liver lobes were removed, measured, photographed, and serially sectioned for hematoxylin and eosin (H&E) staining. The tumor fraction was measured and quantified using the Aperio Imagescope v10.2.2.2319 software, and tumor weight was calculated by multiplying liver weight by the tumor fraction.

PET imaging used to monitor tumor growth was performed in the same manner as described in Experimental Example 6-2.

After monitoring, the animals of the two groups were all euthanized, and the livers of the animals were analyzed to examine whether the results of in vivo image monitoring were consistent with the histopathological findings.

Figure 18:
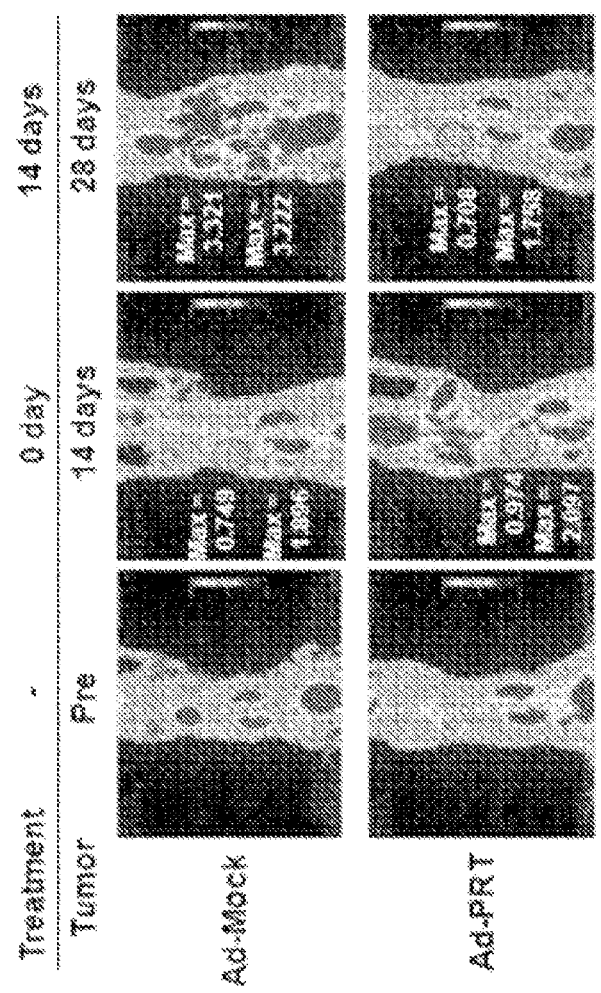
FIG. 18 shows $^{18}$F-FDG PET/CT images taken to measure the therapeutic effect of Ad-PRT. The representative $^{18}$F-FDG PET/CT image of each group is shown together with the $SUV_{max}$ values of the liver.

In the present invention, all the animals were imaged by micro-PET/CT on day 14, and the mice were randomly divided into two groups having similar tumor initiation kinetics based on the spleen uptake of FDG in two different treatments (FIG. 18).

Figure 19:
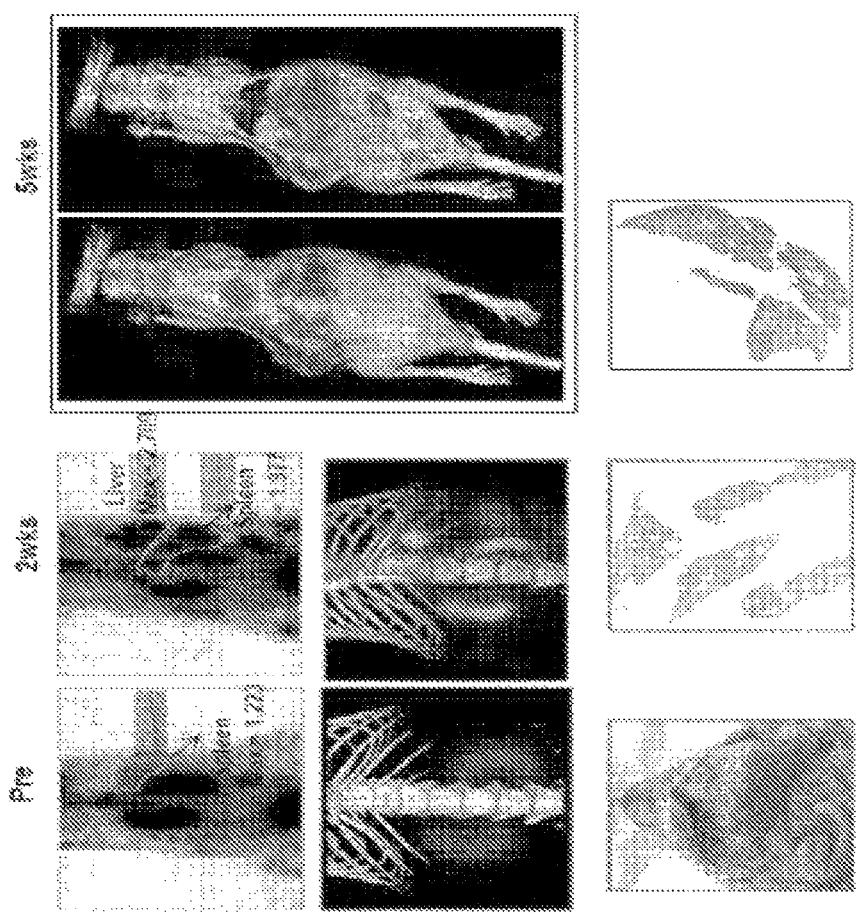
FIG. 19 shows PET/CT images of an Ad-PRT-administered hepatocellular carcinoma mouse model, observed for 5 weeks. Three panels at the bottom show the results of autopsy after 5 weeks, in which the left panel is a photograph of the appearance, the middle panel is a photograph of the left lobe tissue, and the right panel is a photograph of the right lobe tissue. The blue mass is liver cell carcinoma.
Figure 20:
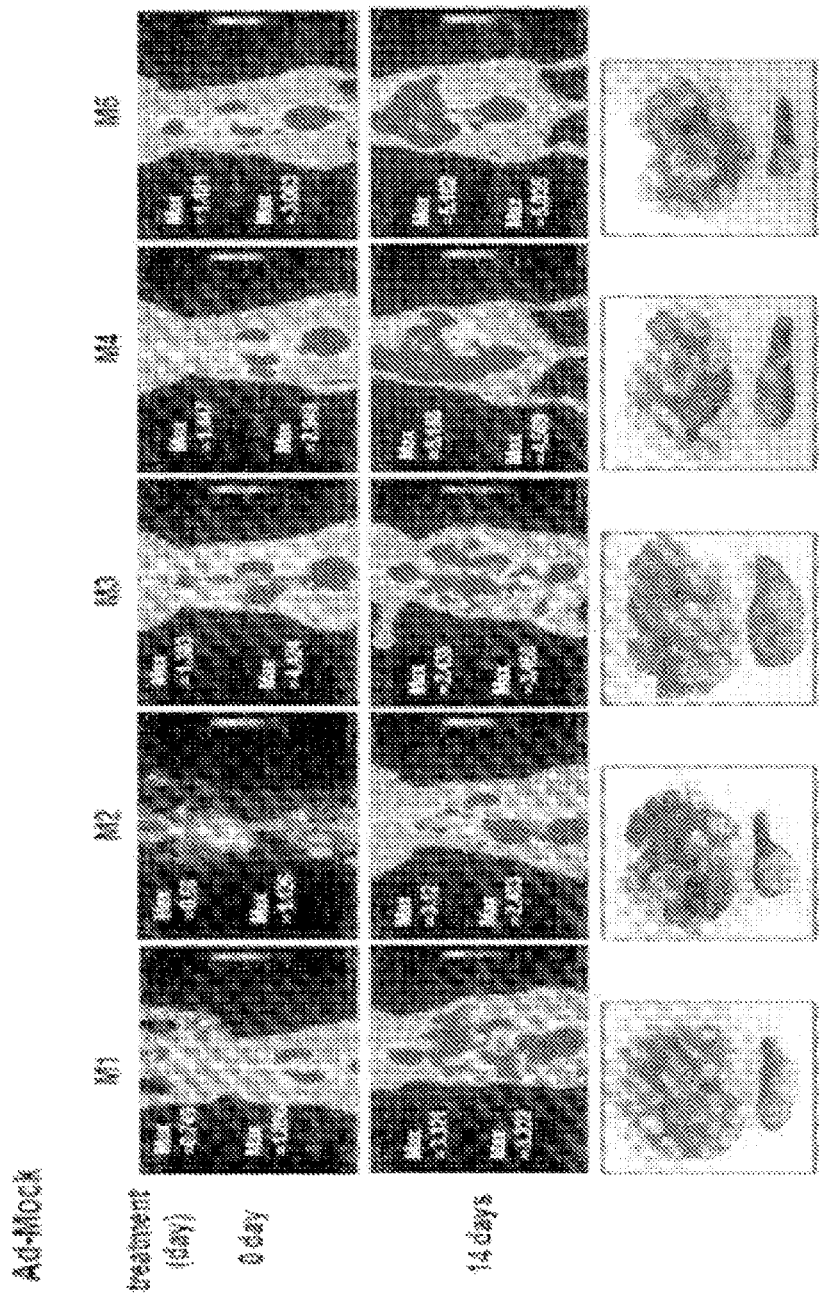
FIG. 20 shows microPET images of an Ad-Mock-administered hepatocellular carcinoma mouse model, observed for 2 weeks.
Figure 21:
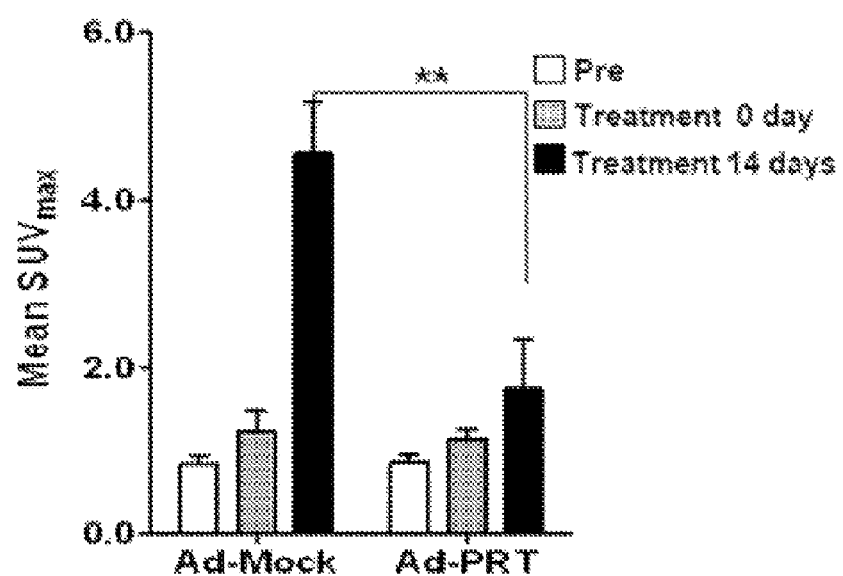
FIG. 21 is a graph showing tumor $SUV_{max}$ values measured in an Ad-Mock group (n=5) and an Ad-PRT group (n=5). The error bar represents mean±SEM (**$p<0.01$).

As a result, as can be seen in FIGS. 19 and 20, the $SUV_{max}$ value of the Ad-PRT-treated group (n=5) was 2.5132±0.194, and the $SUV_{max}$ value of the Ad-Mock-treated group was 2.6916±0.561. At 14 days after treatment with the adenovirus and GCV, the Ad-Mock-treated animals showed 2-4 times stronger [$^{18}$F] FDG PET signals in the liver compared to before the treatment. However, the Ad-PRT-treated mice showed significantly weaker signals compared to the Ad-Mock-treated group (2.195±0.459 vs. 3.850±0.564 in the liver, p=0.00531) (FIG. 21).

Thus, it was found that HSVtk expressed by Ad-PRT in the liver and the spleen stimulates the death of Hep3B liver cancer cells.

Figure 22:
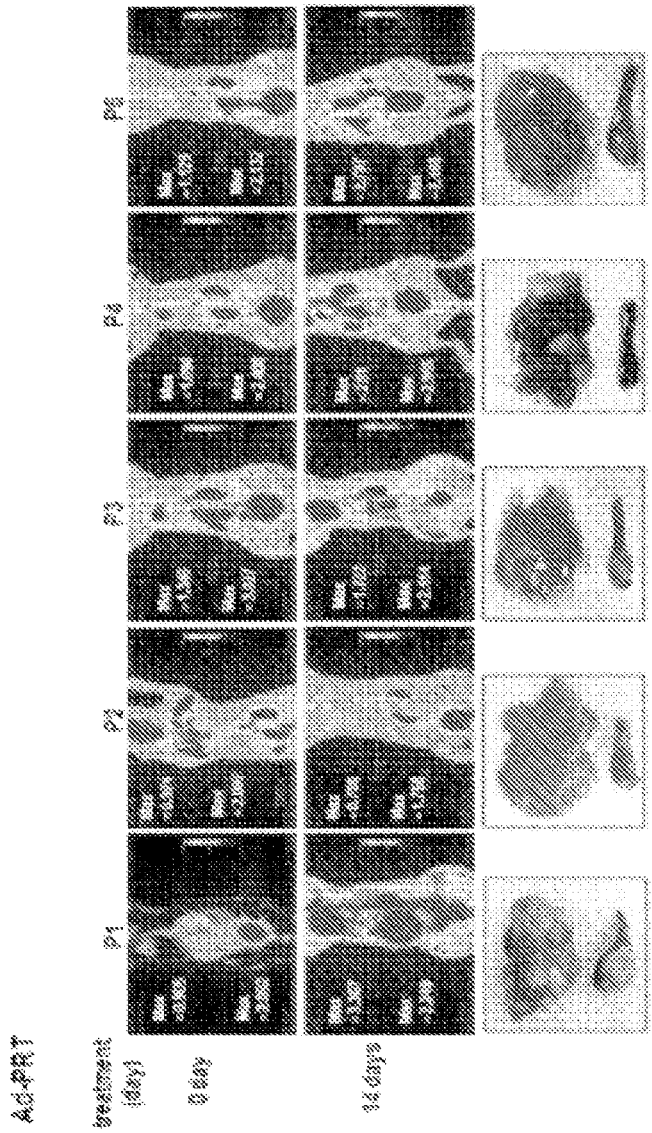
FIG. 22 shows microPET images of an Ad-PRT-administered hepatocellular carcinoma mouse model, observed for 2 weeks.
Figure 23:
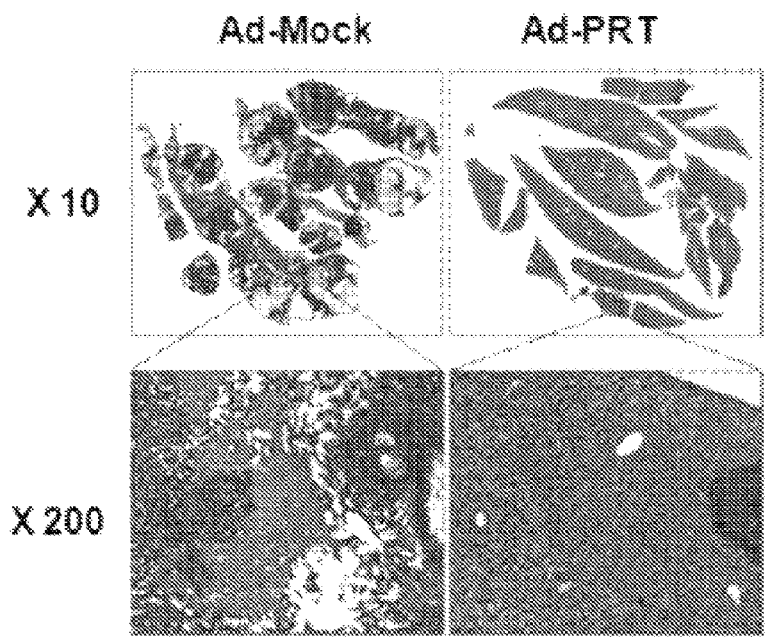
FIG. 23 shows a representative micrograph (H&E staining) of the liver tissue of each group.

In addition, whether the results of in vivo image monitoring of the liver were consistent with the histopathological findings was examined. As a result, as shown in FIGS. 20 and 22 (PET images) and 23 (tissue photographs), the Ad-Mock group showed remarkable abdominal distention. The livers of the control animals were mostly invaded by hepatocellular carcinoma (HCC), whereas the livers of the animals of the Ad-PRT-treated group showed dispersed small light pink tumor nodules as shown in the results of PET imaging. In addition, the multifocal infiltration of homogenous eosinophilic cells that cause rapid tumor growth and tumor embolism could be observed in the animals of the Ad-Mock-treated group, but could not be observed in the Ad-PRT-treated group (FIG. 23).

Figure 24:
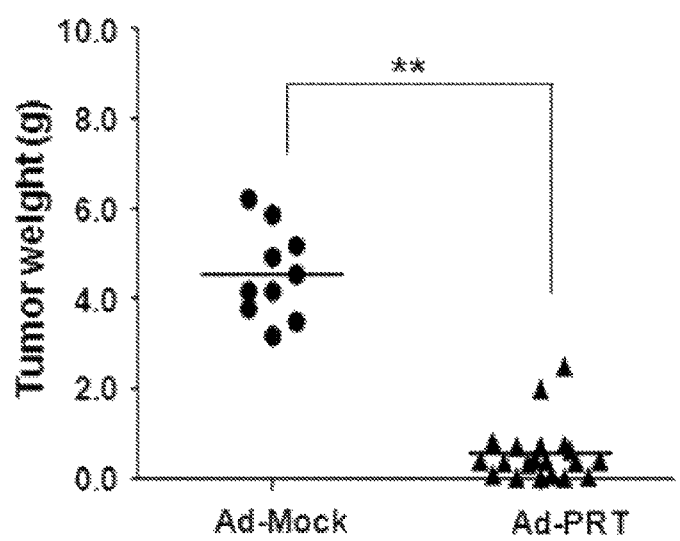
FIG. 24 is a graph showing the tumor weight of each of a PRT group (n=20) and a Mock group (n=10), measured at 14 days after inoculation with tumor cells.

In addition, the tumor weight was calculated by multiplying liver weight by the tumor fraction was 4.60±1.11 in the control group, and 0.49±0.62 in the Ad-PRT-treated group, and thus did significantly differ between the two groups (p=0.00254) (FIG. 24). Therefore, it was found that Ad-PRT exhibits strong anticancer activity against liver cancer.

As described above, the recombinant adenovirus of the present invention includes a liver tissue-specific phosphoenolpyruvate carboxykinase (PEPCK) gene promoter, a trans-splicing ribozyme operably linked to the promoter and acting on a cancer-specific gene, a therapeutic gene or reporter gene linked to the 3' exon of the ribozyme, and a serotype 35 fiber knob and serotype 5 shaft, and lacks adenovirus E1, E3 and E4 orf1 to orf4 genes. It shows significantly high safety in vivo, high specificity for target tissue, and a remarkable anticancer effect, and thus can be effectively used as a gene delivery vector, an anticancer agent or a cancer diagnostic agent.

The invention claimed is:

1. A recombinant adenovirus comprising: a nucleic acid sequence construct comprising a liver specific phosphoenolpyruvate carboxykinase (PEPCK) gene promoter, a trans-splicing ribozyme gene operably linked to the promoter, a therapeutic gene or a reporter gene linked to the 3' exon of the trans-splicing ribozyme gene, a gene enhancer, and a serotype 35 fiber knob and serotype 5 shaft gene, the recombinant adenovirus lacking adenovirus E1, E3 and E4 orf1 to orf4 genes, wherein the gene enhancer is an ApoE (apolipoprotein E) gene enhancer having the nucleotide sequence of SEQ ID NO: 6, a PEPCK gene enhancer, a serum albumin gene enhancer, an AFP (alphafetoprotein) gene enhancer, a CEA (carcinoembryonic antigen) gene enhancer, or a PSA (prostate-specific antigen) gene enhancer; and wherein the trans-splicing ribozyme gene has the nucleotide sequence of SEQ ID NO: 3.

2. The recombinant adenovirus of claim 1, wherein the liver specific PEPCK gene promoter has the nucleotide sequence of SEQ ID NO: 1.

3. The recombinant adenovirus of claim 1, wherein the promoter further comprises an ApoA1 intron having the nucleotide sequence of SEQ ID NO: 2.

4. The recombinant adenovirus of claim 1, wherein the therapeutic gene is selected from the group consisting of drug-sensitizing genes, proapoptotic genes, cytostatic genes, cytotoxic genes, tumor suppressor genes, antigenic genes, cytokine genes, and anti-angiogenic genes.

5. The recombinant adenovirus of claim 1, wherein the reporter gene is a gene that encodes LacZ, CAT (chloramphenicol acetyl transferase), Renila luciferase, firefly luciferase, red fluorescent protein (RFP), green fluorescent protein (GFP), secreted placental alkaline phosphatase (SEAP) or HSV-tk (Herpes simplex virus-thymidine kinase).

6. The recombinant adenovirus of claim 1, wherein the therapeutic gene is a HSV-tk (herpes simplex virus-thymidine kinase) gene having the nucleotide sequence of SEQ ID NO: 4.

7. A pharmaceutical composition for treating liver cancer, which comprises, as an active ingredient, the recombinant adenovirus set forth in claim 1.

8. A composition for diagnosing liver cancer, which comprises, as an active ingredient, the recombinant adenovirus set forth in claim 1.

* * * * *